US009931504B2

(12) United States Patent
Thakkar et al.

(10) Patent No.: US 9,931,504 B2
(45) Date of Patent: Apr. 3, 2018

(54) APPARATUS AND METHODS FOR ASSISTED BREATHING BY TRANSVASCULAR NERVE STIMULATION

(71) Applicant: Simon Fraser University, Burnaby (CA)

(72) Inventors: Viral Thakkar, Burnaby (CA); Joaquin Andres Hoffer, Anmore (CA); Bao Dung Tran, Vancouver (CA); Douglas G. Evans, Downington, PA (US); John Nash, Chester Spring, PA (US)

(73) Assignee: Lungpacer Medical, Inc., Burnaby (CA)

( * ) Notice: Subject to any disclaimer, the term of this patent is extended or adjusted under 35 U.S.C. 154(b) by 0 days.

(21) Appl. No.: 15/370,864

(22) Filed: Dec. 6, 2016

(65) Prior Publication Data

US 2017/0080223 A1    Mar. 23, 2017

Related U.S. Application Data

(63) Continuation of application No. 15/273,196, filed on Sep. 22, 2016, which is a continuation of application
(Continued)

(51) Int. Cl.
*A61N 1/36* (2006.01)
*A61N 1/05* (2006.01)
(Continued)

(52) U.S. Cl.
CPC .......... *A61N 1/3601* (2013.01); *A61B 5/0245* (2013.01); *A61B 5/0422* (2013.01);
(Continued)

(58) Field of Classification Search
CPC ... A61B 5/0245; A61B 5/0422; A61B 5/6852; A61B 2562/043; A61N 1/3601; A61N 1/0551; A61N 1/3611; A61M 25/00
See application file for complete search history.

(56) References Cited

U.S. PATENT DOCUMENTS

| 3,348,548 A | 10/1967 | Chardack |
| 3,470,876 A | 10/1969 | Barchilon |

(Continued)

FOREIGN PATENT DOCUMENTS

| EP | 0 605 796 B1 | 8/2008 |
| EP | 2 489 395 A1 | 8/2012 |

(Continued)

OTHER PUBLICATIONS

Pavlovic, D. et al, "Diaphragm pacing during prolonged mechanical ventilation of the lungs could prevent from respiratory muscle fatigue", Medical Hypotheses, 2003, vol. 60, No. 3, pp. 398-403.

(Continued)

*Primary Examiner* — Catherine Voorhees
(74) *Attorney, Agent, or Firm* — Bookoff McAndrews, PLLC

(57) ABSTRACT

A catheter may include electrodes for transvascular nerve stimulation. The electrodes may be positioned within lumens of the catheter and aligned with apertures in the outer wall of the catheter. The electrodes may produce focused electrical fields for stimulation of one or more nerves. In one embodiment, the catheter may include a set of proximal electrodes and a set of distal electrodes, and the proximal electrodes may stimulate a patient's left phrenic nerve and the distal electrodes may stimulate a patient's right phrenic nerve.

19 Claims, 30 Drawing Sheets

Related U.S. Application Data

No. 14/969,266, filed on Dec. 15, 2015, now Pat. No. 9,545,511, which is a continuation of application No. 14/550,485, filed on Nov. 21, 2014, now Pat. No. 9,242,088.

(60) Provisional application No. 61/907,993, filed on Nov. 22, 2013.

(51) Int. Cl.
| | |
|---|---|
| *A61B 5/042* | (2006.01) |
| *A61M 25/00* | (2006.01) |
| *A61B 5/00* | (2006.01) |
| *A61B 5/0245* | (2006.01) |
| *A61M 25/01* | (2006.01) |

(52) U.S. Cl.
CPC .......... *A61B 5/6852* (2013.01); *A61M 25/00* (2013.01); *A61M 25/0029* (2013.01); *A61M 25/0147* (2013.01); *A61N 1/05* (2013.01); *A61N 1/0551* (2013.01); *A61N 1/3611* (2013.01); *A61N 1/36185* (2013.01); *A61B 2562/043* (2013.01); *A61M 2025/0034* (2013.01)

(56) References Cited

U.S. PATENT DOCUMENTS

| | | | |
|---|---|---|---|
| 3,769,984 | A | 11/1973 | Muench |
| 3,804,098 | A | 4/1974 | Friendman |
| 4,586,923 | A | 5/1986 | Gould et al. |
| 4,860,769 | A | 8/1989 | Fogarty et al. |
| 4,934,049 | A | 6/1990 | Kiekhafer et al. |
| 4,944,088 | A | 7/1990 | Doan et al. |
| 5,042,143 | A | 8/1991 | Holleman et al. |
| 5,056,519 | A | 10/1991 | Vince |
| 5,115,818 | A | 5/1992 | Holleman et al. |
| 5,146,918 | A | 9/1992 | Kallok et al. |
| 5,330,522 | A | 7/1994 | Kreyenhagen |
| 5,345,936 | A | 9/1994 | Pomeranz |
| 5,383,923 | A | 1/1995 | Webster, Jr. |
| 5,411,025 | A | 5/1995 | Webster |
| 5,417,208 | A | 5/1995 | Winkler |
| 5,456,254 | A | 10/1995 | Pietroski et al. |
| 5,465,717 | A | 11/1995 | Imran et al. |
| 5,476,498 | A | 12/1995 | Ayers |
| 5,507,725 | A | 4/1996 | Savage et al. |
| 5,531,686 | A | 7/1996 | Lundquist |
| 5,555,618 | A | 9/1996 | Winkler |
| 5,584,873 | A | 12/1996 | Shoberg et al. |
| 5,678,535 | A | 10/1997 | Dimarco |
| 5,755,765 | A | 5/1998 | Hyde et al. |
| 5,782,828 | A | 7/1998 | Chen et al. |
| RE35,924 | E | 10/1998 | Winkler |
| 6,120,476 | A | 9/2000 | Fung |
| 6,123,699 | A | 9/2000 | Webster, Jr. |
| 6,126,649 | A | 10/2000 | Vantassel et al. |
| 6,171,277 | B1 | 1/2001 | Ponzi |
| 6,183,463 | B1 | 2/2001 | Webster, Jr. |
| 6,198,974 | B1 | 3/2001 | Webster, Jr. |
| 6,212,435 | B1 | 4/2001 | Lattner et al. |
| 6,216,045 | B1 | 4/2001 | Black |
| 6,240,320 | B1 | 5/2001 | Spehr et al. |
| 6,251,126 | B1 | 6/2001 | Ottenhoff et al. |
| 6,269,269 | B1 | 7/2001 | Ottenhoff et al. |
| 6,360,740 | B1 | 3/2002 | Ward et al. |
| 6,415,183 | B1 | 7/2002 | Scheiner et al. |
| 6,449,507 | B1 | 9/2002 | Hill et al. |
| 6,508,802 | B1 | 1/2003 | Rosengart et al. |
| 6,526,321 | B1 | 2/2003 | Spehr et al. |
| 6,569,114 | B2 | 5/2003 | Ponzi et al. |
| 6,585,718 | B2 | 7/2003 | Hayzelden et al. |
| 6,602,242 | B1 | 8/2003 | Fung et al. |
| 6,630,611 | B1 | 10/2003 | Malowaniec |
| 6,682,526 | B1 | 1/2004 | Jones et al. |
| 6,702,780 | B1 | 3/2004 | Gilboa et al. |
| 6,718,208 | B2 | 4/2004 | Hill et al. |
| 6,934,583 | B2 | 8/2005 | Weinberg et al. |
| 6,981,314 | B2 | 1/2006 | Black |
| 6,999,820 | B2 | 2/2006 | Jordan |
| 7,047,627 | B2 | 5/2006 | Black |
| 7,077,823 | B2 | 7/2006 | McDaniel |
| 7,082,331 | B1 | 7/2006 | Park et al. |
| 7,130,700 | B2 | 10/2006 | Gardeski et al. |
| 7,142,903 | B2 | 11/2006 | Rodriguez et al. |
| 7,149,585 | B2 | 12/2006 | Wessman et al. |
| 7,225,016 | B1 | 5/2007 | Koh |
| 7,225,019 | B2 | 5/2007 | Jahns et al. |
| 7,235,070 | B2 | 6/2007 | Vanney |
| 7,269,459 | B1 | 9/2007 | Koh |
| 7,277,757 | B2 | 10/2007 | Casavant et al. |
| 7,283,875 | B2 | 10/2007 | Larsson |
| 7,340,302 | B1 | 3/2008 | Falkenberg et al. |
| 7,363,085 | B1 | 4/2008 | Benser et al. |
| 7,363,086 | B1 | 4/2008 | Koh et al. |
| 7,421,296 | B1 | 9/2008 | Benser et al. |
| 7,519,426 | B1 | 4/2009 | Koh et al. |
| 7,553,305 | B2 | 6/2009 | Honebrink et al. |
| 7,555,349 | B2 | 6/2009 | Wessman et al. |
| 7,591,265 | B2 | 9/2009 | Lee et al. |
| 7,593,760 | B2 | 9/2009 | Rodriguez et al. |
| 7,613,524 | B2 | 11/2009 | Jordan |
| 7,636,600 | B1 | 12/2009 | Koh |
| 7,670,284 | B2 | 3/2010 | Padget et al. |
| 7,672,728 | B2 | 3/2010 | Libbus et al. |
| 7,672,729 | B2 | 3/2010 | Koh et al. |
| 7,771,388 | B2 | 8/2010 | Olsen et al. |
| 7,783,362 | B2 | 8/2010 | Whitehurst et al. |
| 7,797,050 | B2 | 9/2010 | Libbus et al. |
| 7,813,805 | B1 | 10/2010 | Farazi |
| 7,819,883 | B2 | 10/2010 | Westlund et al. |
| 7,840,270 | B2 | 11/2010 | Ignagni et al. |
| 7,853,302 | B2 | 12/2010 | Rodriguez et al. |
| 7,891,085 | B1 | 2/2011 | Kuzma et al. |
| 7,925,352 | B2 | 4/2011 | Stack et al. |
| 7,949,409 | B2 | 5/2011 | Bly |
| 7,962,215 | B2 | 6/2011 | Ignagni et al. |
| 7,970,475 | B2 | 6/2011 | Tehrani et al. |
| 7,972,323 | B1 | 7/2011 | Bencini et al. |
| 7,979,128 | B2 | 7/2011 | Tehrani et al. |
| 8,000,765 | B2 | 8/2011 | Rodriguez et al. |
| 8,021,327 | B2 | 9/2011 | Selkee |
| 8,036,750 | B2 | 10/2011 | Caparso et al. |
| 8,052,607 | B2 | 11/2011 | Byrd |
| 8,104,470 | B2 | 1/2012 | Lee et al. |
| 8,116,872 | B2 | 2/2012 | Tehrani et al. |
| 8,121,692 | B2 | 2/2012 | Haefner et al. |
| 8,135,471 | B2 | 3/2012 | Zhang et al. |
| 8,140,164 | B2 | 3/2012 | Tehrani et al. |
| 8,160,701 | B2 | 4/2012 | Zhao et al. |
| 8,160,711 | B2 | 4/2012 | Tehrani et al. |
| 8,195,297 | B2 | 6/2012 | Penner |
| 8,200,336 | B2 | 6/2012 | Tehrani et al. |
| 8,206,343 | B2 | 6/2012 | Racz |
| 8,233,987 | B2 | 7/2012 | Gelfand et al. |
| 8,233,993 | B2 | 7/2012 | Jordan |
| 8,239,037 | B2 | 8/2012 | Glenn et al. |
| 8,244,358 | B2 | 8/2012 | Tehrani et al. |
| 8,244,359 | B2 | 8/2012 | Gelfand et al. |
| 8,244,378 | B2 | 8/2012 | Bly |
| 8,255,056 | B2 | 8/2012 | Tehrani |
| 8,256,419 | B2 | 9/2012 | Sinderby et al. |
| 8,265,759 | B2 | 9/2012 | Tehrani et al. |
| 8,275,440 | B2 | 9/2012 | Rodriguez et al. |
| 8,280,513 | B2 | 10/2012 | Tehrani et al. |
| 8,335,567 | B2 | 12/2012 | Tehrani et al. |
| 8,348,941 | B2 | 1/2013 | Tehrani |
| 8,369,954 | B2 | 2/2013 | Stack et al. |
| 8,401,640 | B2 | 3/2013 | Zhao et al. |
| 8,401,651 | B2 | 3/2013 | Caparso et al. |
| 8,406,885 | B2 | 3/2013 | Ignagni et al. |
| 8,412,331 | B2 | 4/2013 | Tehrani et al. |
| 8,412,350 | B2 | 4/2013 | Bly |

(56) References Cited

U.S. PATENT DOCUMENTS

| | | | |
|---|---|---|---|
| 8,428,711 B2 | 4/2013 | Lin et al. |
| 8,428,726 B2 | 4/2013 | Ignagni et al. |
| 8,433,412 B1 | 4/2013 | Westlund et al. |
| 8,467,876 B2 | 6/2013 | Tehrani |
| 8,473,068 B2 | 6/2013 | Farazi |
| 8,478,412 B2 | 7/2013 | Ignagni et al. |
| 8,478,413 B2 | 7/2013 | Karamanoglu et al. |
| 8,478,426 B2 | 7/2013 | Barker |
| 8,483,834 B2 | 7/2013 | Lee et al. |
| 8,504,158 B2 | 8/2013 | Karamanoglu et al. |
| 8,509,901 B2 | 8/2013 | Tehrani |
| 8,509,902 B2 | 8/2013 | Cho et al. |
| 8,509,919 B2 | 8/2013 | Yoo et al. |
| 8,522,779 B2 | 9/2013 | Lee et al. |
| 8,560,072 B2 | 10/2013 | Caparso et al. |
| 8,617,228 B2 | 12/2013 | Wittenberger et al. |
| 8,620,450 B2 | 12/2013 | Tockman et al. |
| 8,626,292 B2 | 1/2014 | McCabe et al. |
| 8,630,707 B2 | 1/2014 | Zhao et al. |
| 8,676,323 B2 | 3/2014 | Ignagni et al. |
| 8,696,656 B2 | 4/2014 | Abboud et al. |
| 8,706,223 B2 | 4/2014 | Zhou et al. |
| 8,706,235 B2 | 4/2014 | Karamanoglu et al. |
| 8,706,236 B2 | 4/2014 | Ignagni et al. |
| 8,718,763 B2 | 5/2014 | Zhou et al. |
| 8,725,259 B2 | 5/2014 | Kornet et al. |
| 8,755,889 B2 | 6/2014 | Scheiner |
| 8,781,578 B2 | 7/2014 | McCabe et al. |
| 8,781,582 B2 | 7/2014 | Ziegler et al. |
| 8,781,583 B2 | 7/2014 | Cornelussen et al. |
| 8,838,245 B2 | 9/2014 | Lin et al. |
| 8,897,879 B2 | 11/2014 | Karamanoglu et al. |
| 8,903,509 B2 | 12/2014 | Tockman et al. |
| 8,909,341 B2 | 12/2014 | Gelfand et al. |
| 8,914,113 B2 | 12/2014 | Zhang et al. |
| 8,942,824 B2 | 1/2015 | Yoo et al. |
| 9,042,981 B2 | 5/2015 | Yoo et al. |
| 2003/0195571 A1 | 10/2003 | Burnes et al. |
| 2004/0077936 A1 | 4/2004 | Larsson |
| 2004/0088015 A1 | 5/2004 | Casavant et al. |
| 2004/0186543 A1 | 9/2004 | King et al. |
| 2005/0004565 A1 | 1/2005 | Vanney |
| 2005/0013879 A1 | 1/2005 | Lin et al. |
| 2005/0043765 A1 | 2/2005 | Williams et al. |
| 2005/0138791 A1 | 6/2005 | Black et al. |
| 2005/0138792 A1 | 6/2005 | Black |
| 2005/0165457 A1 | 7/2005 | Benser et al. |
| 2005/0192655 A1 | 9/2005 | Black |
| 2005/0251238 A1 | 11/2005 | Wallace et al. |
| 2006/0058852 A1 | 3/2006 | Koh et al. |
| 2006/0149334 A1 | 7/2006 | Tehrani et al. |
| 2006/0217791 A1 | 9/2006 | Spinka et al. |
| 2006/0229677 A1 | 10/2006 | Moffitt et al. |
| 2006/0253161 A1 | 11/2006 | Libbus et al. |
| 2007/0005053 A1 | 1/2007 | Dando |
| 2007/0027448 A1 | 2/2007 | Paul et al. |
| 2007/0168007 A1 | 7/2007 | Kuzma et al. |
| 2007/0208388 A1 | 9/2007 | Jahns et al. |
| 2007/0250056 A1 | 10/2007 | Vanney |
| 2007/0255379 A1 | 11/2007 | Williams et al. |
| 2008/0161878 A1 | 7/2008 | Tehrani et al. |
| 2008/0177347 A1 | 7/2008 | Tehrani et al. |
| 2008/0183186 A1 | 7/2008 | Bly et al. |
| 2008/0183187 A1 | 7/2008 | Bly |
| 2008/0183239 A1 | 7/2008 | Tehrani et al. |
| 2008/0183240 A1 | 7/2008 | Tehrani et al. |
| 2008/0183253 A1 | 7/2008 | Bly |
| 2008/0183255 A1 | 7/2008 | Bly et al. |
| 2008/0183259 A1 | 7/2008 | Bly et al. |
| 2008/0183264 A1 | 7/2008 | Bly et al. |
| 2008/0183265 A1 | 7/2008 | Bly et al. |
| 2008/0188903 A1 | 8/2008 | Tehrani et al. |
| 2008/0215106 A1 | 9/2008 | Lee et al. |
| 2008/0288010 A1 | 11/2008 | Tehrani et al. |
| 2008/0288015 A1 | 11/2008 | Tehrani et al. |
| 2008/0312712 A1 | 12/2008 | Penner |
| 2008/0312725 A1 | 12/2008 | Penner |
| 2009/0036947 A1 | 2/2009 | Westlund et al. |
| 2010/0022950 A1* | 1/2010 | Anderson ......... A61B 1/00114 604/100.01 |
| 2010/0036451 A1 | 2/2010 | Hoffer |
| 2010/0077606 A1 | 4/2010 | Black et al. |
| 2010/0114227 A1 | 5/2010 | Cholette |
| 2010/0268311 A1 | 10/2010 | Cardinal et al. |
| 2011/0077726 A1 | 3/2011 | Westlund et al. |
| 2011/0118815 A1 | 5/2011 | Kuzma et al. |
| 2011/0230932 A1 | 9/2011 | Tehrani et al. |
| 2011/0288609 A1 | 11/2011 | Tehrani et al. |
| 2012/0053654 A1 | 3/2012 | Tehrani et al. |
| 2012/0158091 A1 | 6/2012 | Tehrani et al. |
| 2012/0209284 A1 | 8/2012 | Westlund et al. |
| 2012/0215278 A1 | 8/2012 | Penner |
| 2012/0323293 A1 | 12/2012 | Tehrani et al. |
| 2013/0018247 A1 | 1/2013 | Glenn et al. |
| 2013/0018427 A1 | 1/2013 | Pham et al. |
| 2013/0023972 A1 | 1/2013 | Kuzma et al. |
| 2013/0030496 A1 | 1/2013 | Karamanoglu et al. |
| 2013/0030497 A1 | 1/2013 | Karamanoglu et al. |
| 2013/0060245 A1 | 3/2013 | Grunewald et al. |
| 2013/0116743 A1 | 5/2013 | Karamanoglu et al. |
| 2013/0131743 A1* | 5/2013 | Yamasaki ......... A61B 18/1492 607/3 |
| 2013/0158625 A1 | 6/2013 | Gelfand et al. |
| 2013/0165989 A1 | 6/2013 | Gelfand et al. |
| 2013/0167372 A1 | 6/2013 | Black |
| 2013/0197601 A1 | 8/2013 | Tehrani et al. |
| 2013/0289686 A1 | 10/2013 | Masson et al. |
| 2013/0296964 A1 | 11/2013 | Tehrani |
| 2013/0296973 A1 | 11/2013 | Tehrani et al. |
| 2013/0317587 A1* | 11/2013 | Barker ................. A61N 1/0551 607/118 |
| 2013/0333696 A1 | 12/2013 | Lee et al. |
| 2014/0088580 A1 | 3/2014 | Wittenberger et al. |
| 2014/0114371 A1 | 4/2014 | Westlund et al. |
| 2014/0128953 A1 | 5/2014 | Zhao et al. |
| 2014/0148780 A1 | 5/2014 | Putz |
| 2014/0316486 A1 | 10/2014 | Zhou et al. |
| 2014/0324115 A1 | 10/2014 | Ziegler et al. |
| 2015/0034081 A1 | 2/2015 | Tehrani et al. |
| 2015/0045810 A1 | 2/2015 | Hoffer et al. |
| 2015/0045848 A1 | 2/2015 | Cho et al. |
| 2015/0119950 A1 | 4/2015 | Demmer et al. |
| 2015/0165207 A1* | 6/2015 | Karamanoglu ...... A61N 1/3601 600/374 |
| 2015/0265833 A1 | 9/2015 | Meyyappan et al. |
| 2015/0374252 A1* | 12/2015 | de la Rama ......... A61B 5/0422 600/374 |

FOREIGN PATENT DOCUMENTS

| | | |
|---|---|---|
| WO | 2009/006337 A1 | 1/2009 |
| WO | WO 2008/092246 A1 | 8/2009 |
| WO | WO 2012/106533 A2 | 8/2012 |
| WO | 2013/131187 A1 | 9/2013 |

OTHER PUBLICATIONS

Extended European Search Report issued in EP App. No. 14864542.7, dated Jun. 2, 2017 (8 pages).

\* cited by examiner

Fig. 12A
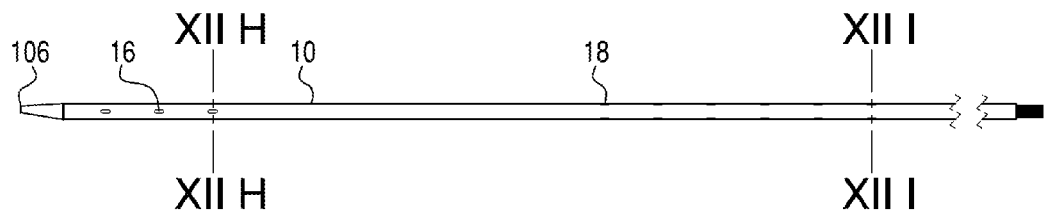
Fig. 12B
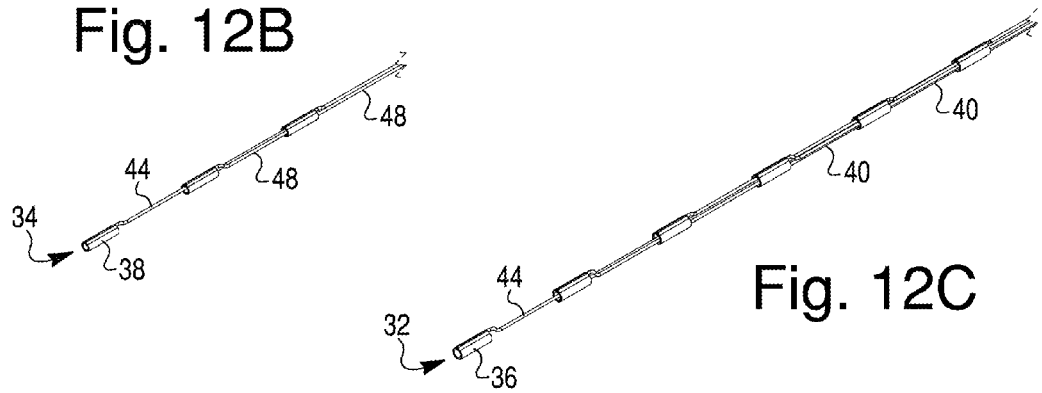
Fig. 12C
Fig. 12D
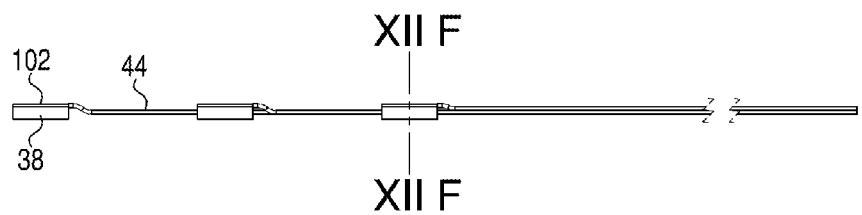
Fig. 12E
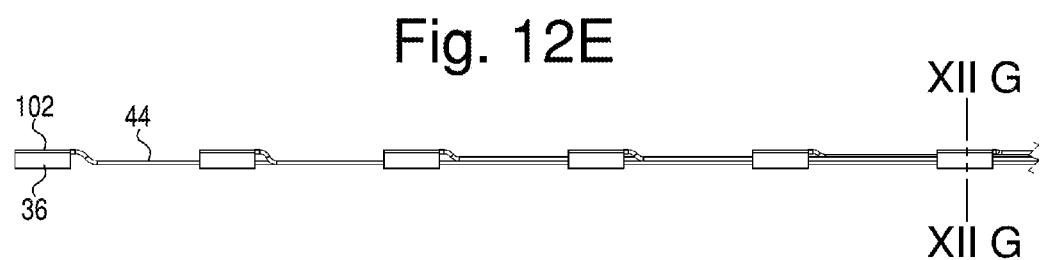

Fig. 18A
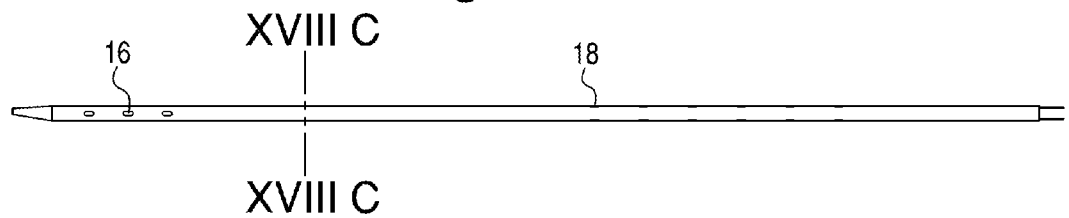
Fig. 18B
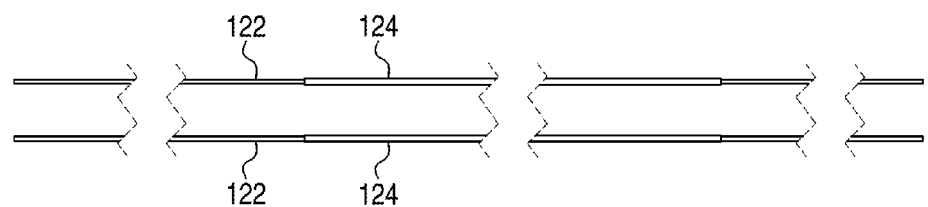
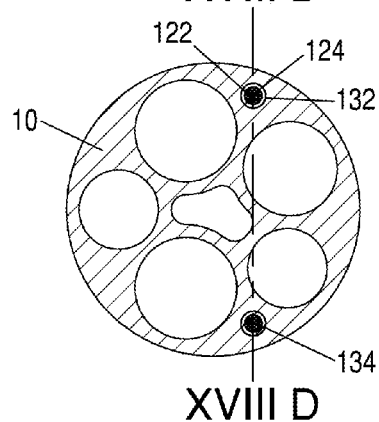
Fig. 18C
Fig. 18D
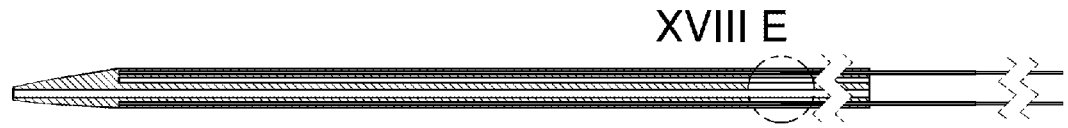

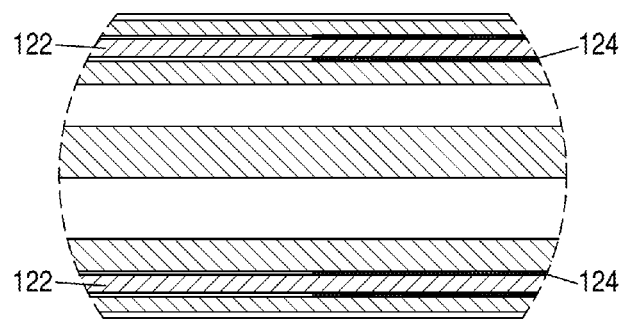
Fig. 18E
Fig. 19A
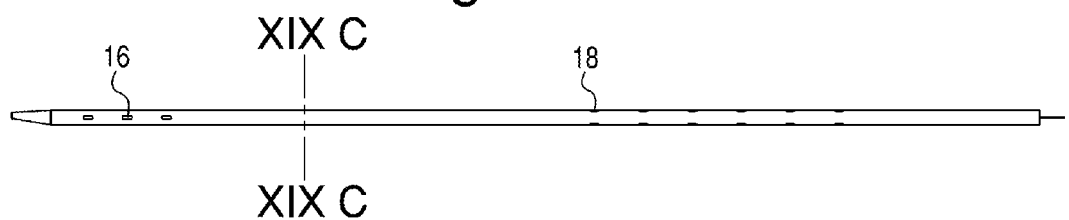
Fig. 19B
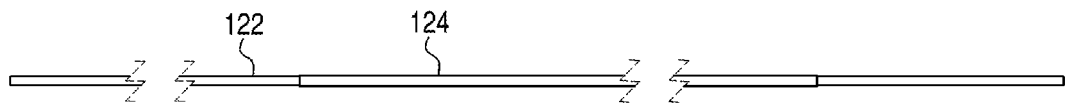
Fig. 19C
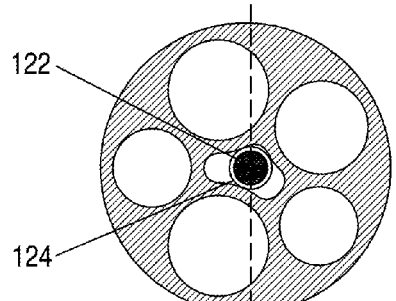

Fig. 26A
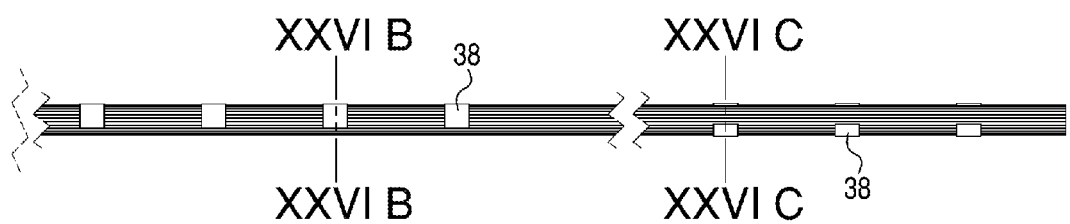
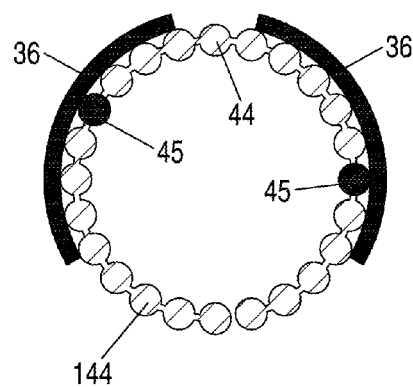
Fig. 26B
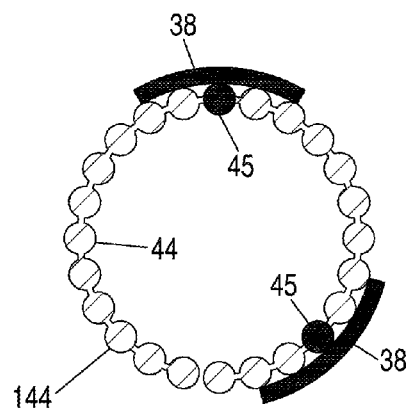
Fig. 26C

APPARATUS AND METHODS FOR ASSISTED BREATHING BY TRANSVASCULAR NERVE STIMULATION

CROSS-REFERENCE TO RELATED APPLICATIONS

This application is a continuation application of U.S. patent application Ser. No. 15/273,196, which is a continuation application of U.S. patent application Ser. No. 14/969,266, filed Dec. 15, 2015, which is a continuation application of U.S. patent application Ser. No. 14/550,485, filed Nov. 21, 2014, now U.S. Pat. No. 9,242,088, issued Jan. 26, 2016, which claims the benefit of U.S. Provisional Patent Application No. 61/907,993, filed Nov. 22, 2013. Each of the above-referenced applications is incorporated herein by reference in its entirety.

TECHNICAL FIELD

Embodiments of this disclosure relate to medical apparatus and particularly to apparatus applicable for the restoration, enhancement, or modulation of diminished neurophysiological functions. Specific embodiments provide apparatus for stimulating the diaphragm muscle to assist breathing by trans vascular electrical stimulation of nerves.

BACKGROUND

Electrical stimulation of nerves is widely applied in the treatment of a range of conditions and may be applied to control muscle activity or to generate sensations. Nerves may be stimulated by placing electrodes in, around, or near the nerves and activating the electrodes by means of an implanted or external source of electricity.

The phrenic nerves normally transmit signals from the brain that cause the contractions of the diaphragm necessary for breathing. However, various conditions can prevent appropriate signals from being delivered to the phrenic nerves. These include:

permanent or temporary injury or disease affecting the spinal cord or brain stem;

Amyotrophic Lateral Sclerosis (ALS);

decreased day or night ventilatory drive (e.g. central sleep apnea, Ondine's curse); and decreased ventilatory drive while under the influence of anesthetic agents and/or mechanical ventilation.

These conditions affect a significant number of people.

Intubation and positive pressure mechanical ventilation (MV) may be used for periods of several hours or several days, sometimes weeks, to help critically ill patients breathe while in intensive care units (ICU). Some patients may be unable to regain voluntary breathing and thus require prolonged or permanent mechanical ventilation. Although mechanical ventilation can be initially lifesaving, it has a range of significant problems and/or side effects. Mechanical ventilation:

often causes ventilator-induced lung injury (VILI) and alveolar damage which can lead to accumulation of fluid in the lungs and increased susceptibility to infection (ventilator-associated pneumonia; VAP);

commonly requires sedation to reduce discomfort and anxiety in acutely intubated patients;

causes rapid atrophy of the disused diaphragm muscle (ventilator-induced diaphragm dysfunction, VIDD);

can adversely affect venous return because the lungs are pressurized and the diaphragm is inactive;

interferes with eating and speaking;

requires apparatus that is not readily portable; and increases the risk of dying if the patient fails to regain normal breathing and becomes ventilator-dependent.

A patient who is sedated and connected to a mechanical ventilator cannot breathe normally because the central neural drive to the diaphragm and accessory respiratory muscles is suppressed. Inactivity leads to muscle disuse atrophy and an overall decline in well-being. Diaphragm muscle atrophy occurs rapidly and can be a serious problem to the patient. According to a published study in organ donor patients (Levine et al., New England Journal of Medicine, 358: 1327-1335, 2008) after only 18 to 69 hours of mechanical ventilation, all diaphragm muscle fibers had shrunk on average by 52-57%. Muscle fiber atrophy results in muscle weakness and increased fatigability. Therefore, ventilator-induced diaphragm atrophy could cause a patient to become ventilator-dependent. It has been reported that over 840,000 ICU patients in the United States, Europe and Canada become ventilator dependent every year.

There remains a need for cost-effective, practical, surgically simple and minimally invasive apparatus and methods that may be applied to stimulate breathing. There is also a need for apparatus and methods for facilitating patients on MV to regain the capacity to breathe naturally and to be weaned from MV.

SUMMARY

Embodiments of the present disclosure relate to, among other things, medical apparatus and methods for nerve stimulation. Specific embodiments provide apparatus for stimulating breathing by transvascular electrical stimulation of nerves. Each of the embodiments disclosed herein may include one or more of the features described in connection with any of the other disclosed embodiments.

In one embodiment, a catheter may include an elongated tubular member including a first aperture and a second aperture each in an exterior wall of the elongated tubular member; a first electrode located within the elongated tubular member and positioned relative to the first aperture so that electrical energy associated with the first electrode travels to or from the exterior of the elongated tubular member through the first aperture; and a second electrode located within the elongated tubular member and positioned relative to the second aperture so that electrical energy associated with the second electrode travels to or from the exterior of the elongated tubular member through the second aperture.

The catheter may additionally or alternatively include one or more of the following features: a plane that is perpendicular to the longitudinal axis of the catheter may pass through both the first and second apertures; a plane that is perpendicular to the longitudinal axis of the catheter and that passes through the first aperture does not pass through the second aperture; a line parallel to the longitudinal axis of the catheter may pass through both the first and second apertures; the catheter may further include a third aperture and a fourth aperture each in the exterior wall of the elongated tubular member located proximate to a distal end of the catheter, and the first and second apertures may be located proximal to the third and fourth apertures, a third electrode located within the elongated tubular member and positioned relative to the third aperture so that electrical energy associated with the third electrode travels to or from the exterior of the elongated tubular member through the third aperture, and a fourth electrode located within the elongated tubular member and positioned relative to the fourth aperture so that electrical energy associated with the fourth electrode travels to or from the exterior of the elongated tubular member through the fourth aperture; a plane crossing a longitudinal axis of the catheter may pass through both the first and second electrodes to define a cross-sectional area of the catheter, and the cross-sectional area does not include any other electrodes; the first and second electrodes may be bipolar electrodes configured to stimulate a nerve; the first and second apertures and the first and second electrodes may be arranged such that activation of the first and second electrodes creates an electrical field extending radially outwards from only a portion of a circumference of the catheter; and the catheter may further include a first electrode assembly extending through a first lumen of the catheter and a second electrode assembly extending through a second lumen of the catheter, and the first electrode assembly may include the first electrode and the second electrode assembly may include the second electrode.

In another embodiment, a catheter may include an elongated tubular member including a first plurality of apertures in an exterior wall of the elongated tubular member and a second plurality of apertures in the exterior wall, wherein the second plurality of apertures may be located distal to the first plurality of apertures such that a longitudinal distance between a most distal aperture of the first plurality of apertures and a most proximal aperture of the second plurality of apertures is greater than a longitudinal distance between adjacent apertures of the first plurality of apertures and a longitudinal distance between adjacent apertures of the second plurality of apertures; a plurality of proximal electrodes located within the elongated tubular member, wherein each of the plurality of proximal electrodes may be positioned radially inward of a corresponding one of the first plurality of apertures; and a plurality of distal electrodes located within the elongated tubular member, wherein each of the plurality of distal electrodes may be positioned radially inward of a corresponding one of the second plurality of apertures.

The catheter may additionally or alternatively include one or more of the following features: the first plurality of apertures may include at least three apertures, and the second plurality of apertures may include at least three apertures; the first plurality of apertures may be arranged in two rows extending in a proximal-distal direction along the catheter; the second plurality of apertures may be arranged in two rows extending in a proximal-distal direction along the catheter, and lines parallel to a longitudinal axis of the catheter and passing through the two rows of the second plurality of apertures do not pass through the two rows of the first plurality of apertures; the first plurality of apertures may include pairs of apertures, and each pair of apertures may be arranged such that a plane passing through the centers of the pair of apertures forms an acute angle with respect to a plane passing perpendicular to a longitudinal axis of the catheter; the first plurality of apertures may include pairs of apertures, and each pair of apertures may be arranged such that a plane passing through the centers of the two apertures is perpendicular to a longitudinal axis of the catheter; a pair of the plurality of proximal electrodes may include bipolar electrodes configured to stimulate a first nerve, and a pair of the plurality of distal electrodes includes bipolar electrodes configured to stimulate a second nerve; bipolar electrode pairs of the plurality of proximal electrodes may be configured to be selectively activated to create an electrical field extending radially outwards from only a portion of a circumference of a longitudinal section of the catheter that includes the proximal electrodes, and bipolar electrode pairs of the plurality of distal electrodes may be configured to be selectively activated to create an electrical field extending radially outwards from only a portion of the circumference of a longitudinal section of the catheter that includes the distal electrodes; the catheter may further include a first electrode assembly and a second electrode assembly; each of the first and second electrode assemblies may include half of the plurality of proximal electrodes; the catheter may further include a third electrode assembly and a fourth electrode assembly; each of the third and fourth electrode assemblies may include half of the plurality of distal electrodes; the catheter may include a first lumen, a second lumen, a third lumen, and a fourth lumen; the first electrode assembly may be located within the first lumen, the second electrode assembly may be located within the second lumen, the third electrode assembly may be located within the third lumen, and the fourth electrode assembly may be located within the fourth lumen; and each of the proximal and distal electrodes may be electrically coupled to a distal end of an elongated conductive member.

In yet another embodiment, a catheter may include an elongated member; a proximal set of electrodes positioned along a first longitudinal portion of the elongated member to at least one of emit or receive electrical energy to or from an exterior of the elongated member along only a portion of a circumference of the first longitudinal portion; and a distal set of electrodes positioned along a second longitudinal portion of the elongated member to at least one of emit or receive electrical energy to or from an exterior of the elongated member along only a portion of a circumference of the second longitudinal portion. The proximal and distal sets of electrodes may be positioned such that the proximal set of electrodes is configured to stimulate a patient's left phrenic nerve and the distal set of electrodes is configured to stimulate the patient's right phrenic nerve.

The catheter may additionally or alternatively include one or more of the following features: each of the proximal and distal electrodes may include a conductive tubular member; each of the proximal and distal electrodes may include an arcuate member having an inner wall and an outer wall; each of the proximal and distal electrodes may be electrically coupled to an elongated conductive member that extends proximally from the electrode; the proximal and distal electrodes may be electrically coupled to the distal ends of the elongated conductive members; at least one of the proximal and distal electrodes may include conductive ink printed on an exterior of the elongated member; the elongated member of the catheter may include a first lumen, a second lumen, a third lumen, and a fourth lumen; a first plurality of the proximal set of electrodes may be supported by a first elongated tubular member within the first lumen; a second plurality of the proximal set of electrodes may be supported by a second elongated tubular member within the second lumen; a first plurality of the distal set of electrodes may be supported by a third elongated tubular member within the third lumen; and a second plurality of the distal set of electrodes may be supported by a fourth elongated tubular member within the fourth lumen; at least one of the proximal and distal electrodes may include a conductive member fixed to an exterior of the elongated member; the catheter may further include a steering mechanism adapted to deflect a distal end of the elongated member; the catheter may further include a ribbon cable having a plurality of elongated conductive members; and a proximal portion of the catheter may include a first cross-sectional shape, and a distal portion of the catheter may include a second cross-sectional shape different than the first cross-sectional shape.

Further aspects of the disclosures and features of example embodiments are illustrated in the appended drawings and/or described in the text of this specification and/or described in the accompanying claims. It may be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate non-limiting exemplary embodiments of the present disclosure and together with the description serve to explain the principles of the disclosure.

16B illustrates a transverse cross-section of the catheter of FIG. 16A showing the steering mechanism in a central lumen.

FIG. 18A illustrates a catheter having a steering mechanism that includes diametric lumens, each with a pull wire; FIG. 18B illustrates the pull wires of the steering mechanism; FIG. 18C illustrates a transverse cross-sectional view of the catheter of FIG. 18A; FIG. 18D illustrates a longitudinal cross-sectional view of the distal portion of the catheter of FIG. 18A showing the steering mechanism; and FIG. 18E illustrates an exploded view of a portion of the steering mechanism shown in FIG. 18D, according to exemplary embodiments.

FIG. 19A illustrates a catheter having a steering mechanism that includes a single push/pull wire inserted through a hypodermic tube/compression coil and adhered within a central lumen; FIG. 19B illustrates the steering mechanism; FIG. 19C illustrates a transverse cross-sectional view of the catheter of FIG. 19A.

FIG. 26A illustrates electrodes attached to a ribbon wire catheter; FIG. 26B illustrates a cross-sectional view of a proximal electrode pair of the catheter of FIG. 26A; FIG. 26C illustrates a cross-sectional view of a distal electrode pair of the catheter of FIG. 26A.

DETAILED DESCRIPTION

Figure 1A:
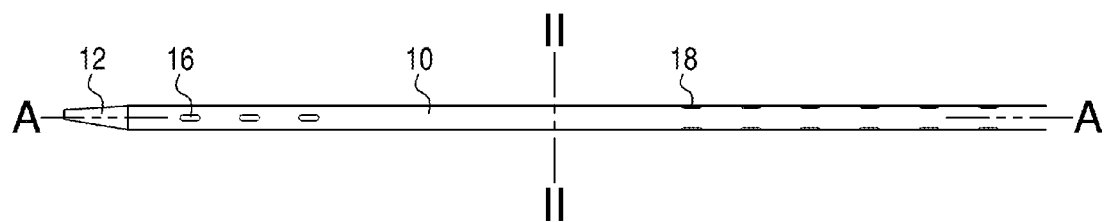
FIGS. 1A, 1B, and 1C illustrate various views of a catheter having windows that may align with nerve-stimulating electrodes within the catheter, according to an exemplary embodiment.

Throughout the following description, specific details are set forth to provide a more thorough understanding to persons skilled in the art. The following description of examples of the technology is not intended to be exhaustive or to limit the system to the precise forms of any example embodiment. Accordingly, the description and drawings are to be regarded in an illustrative, rather than a restrictive, sense.

General Overview

In general, embodiments of this disclosure relate to medical devices and methods for electrically stimulating a patient's nerves. In one embodiment, the patient's nerves may be stimulated to activate the diaphragm to restore or control breathing.

The medical devices described herein may include several components, including a catheter having an elongated tubular member and one or more electrode assemblies, a signal generator to provide stimulation energy to the electrode assemblies, and one or more sensors to sense the condition of the patient and adjust the stimulation signals. The medical devices may further include a steering mechanism. Various embodiments of catheters are disclosed, including windowed catheters, multi-lumen catheters, and ribbon catheters. In addition, various embodiments of electrode assemblies are disclosed, which may be used alone, in combination with other electrode assemblies, and with any of the disclosed elongated tubular members that form the outer portion of the catheters. The term "catheter" may used herein to refer to the elongated tubular member of the catheter or to the assembled catheter as a whole, which may include electrode assemblies, a steering mechanism, and any other components within or coupled to the elongated tubular member. Several types of steering mechanisms are also described.

The different embodiments of the various medical device components (e.g., catheters, electrode assemblies, steering mechanisms, etc.) may be combined and used together in any logical arrangement. Furthermore, individual features or elements of any described embodiment may be combined with or used in connection with the individual features or elements of other embodiments. The various embodiments may further be used in different contexts than those specifically described herein. For example, the disclosed electrode structures may be combined or used in combination with various deployment systems known in the art for various diagnostic and/or therapeutic applications.

During use, the medical devices (e.g., a catheter with one or more electrode assemblies) may be inserted into a patient's blood vessels such that the electrode assemblies are near the patient's nerves. The electrode assemblies may then be used for transvascular electrical stimulation of the patient's nerves. The disclosed devices may be optimized for rapid, temporary deployment in a patient and easy removal from the patient. The disclosed devices may be used, for example, for restoring breathing, treating conditions such as disuse muscle atrophy and chronic pain, or for any other procedures involving nerve stimulation. The disclosed devices may be used to treat acute or chronic conditions.

Medical Device Overview: Catheter and Electrode Assemblies

Referring to FIGS. 1-6B, an overview of an exemplary embodiment of a medical device and a method of use will be described. Later drawings will be referenced to describe additional or alternative embodiments of the various medical device components.

Figure 1B:
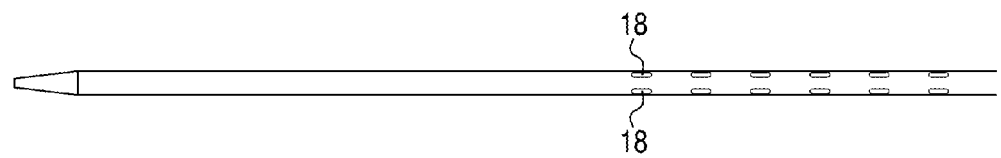
Figure 1C:
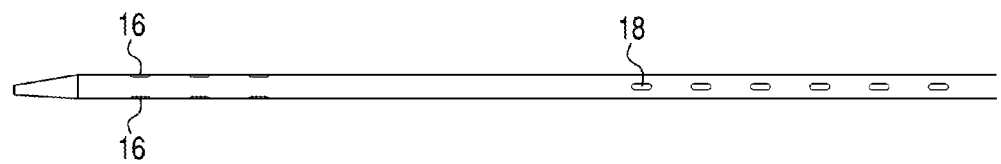

FIGS. 1A, 1B, and 1C illustrate various views of a catheter 10 according to an exemplary embodiment. In FIGS. 1A, 1B, and 1C, the catheter 10 is shown in a different rotational position around a longitudinal axis A-A through the catheter 10. The catheter 10 may include an elongated tubular member made of extruded polyurethane (or any other suitable biocompatible material). As can be seen in FIG. 1A, the catheter 10 may include a row of distal windows 16, which may be aligned along a longitudinal axis near a distal end 12 of the catheter 10. The catheter 10 may further include a second row of distal windows 16, which can be partially seen in FIG. 1C. At a position on the catheter 10 proximal to windows 16 (in some cases at the proximal end of the catheter 10), the catheter 10 may similarly include two rows of proximal windows 18. These windows will be referred to herein as "proximal windows 18" to distinguish the proximal set of windows 18 from the distal set of windows 16. In other embodiments, the catheter 10 may include three or more rows of distal windows 16 or three or more rows of proximal windows 18. The proximal windows 18 may have the same or different structural features as the distal windows 16. A section of the catheter 10 between the proximal windows 18 and the distal windows 16 may be free of windows.

In one embodiment, the catheter 10 includes six distal windows 16 and twelve proximal windows 18. However, in other embodiments, the catheter 10 may include fewer or more proximal or distal windows. For example, in other embodiments, the catheter 10 may include two, four, eight, ten, twelve, or more distal windows 16, and/or two, four, six, eight, ten, or more than twelve proximal windows 18. The distal windows 16 and proximal windows 18 may be configured in pairs such that the catheter 10 has an even number of distal windows 16 and an even number of proximal windows 18. However, the number of windows 16 or 18 may also be an odd number.

The windows 16, 18 may be cut (e.g. by a laser, manual skive, drill, punch, etc.) through the exterior wall of catheter 10, or the windows may be formed by any other suitable method, such as during an extrusion process or other manufacturing process. The windows 16, 18 may be elongated along the longitudinal axis A-A. They may have a rectangular, oval, square, or any other shape. The windows 16, 18 may be apertures configured to allow electrical signals to travel from an interior lumen of the catheter 10 to the exterior of the catheter 10. In an additional or alternative embodiment, the windows 16, 18 may be covered by a material that allows electrical signals to pass through. As can be seen in the figures, the proximal windows 18 may be rotationally offset from the distal windows 16. In other words, in one embodiment, a straight line drawn proximally through a row of distal windows 16 does not pass through a row of proximal windows 18. In other embodiments, one or more rows of proximal windows 18 may be aligned with a corresponding row of distal windows 16.

The dimensions of catheter 10 may be customized in accordance with the anatomy of a particular patient. However, in some embodiments, the length of the section of the catheter 10 that includes the proximal windows 18 may be 10 cm or less, between 3-5 cm, or between 1-3 cm. The distance between two adjacent proximal windows 18 (whether the windows are longitudinally adjacent or adjacent on the same row of windows) may be 5 cm or less, 3 cm or less, or may be around 1 cm. The length of the section of the catheter 10 that includes the distal windows 16 may be 6 cm or less, between 2-4 cm, or between 1-2 cm. The distance between two adjacent distal windows 16 (whether longitudinally adjacent or adjacent on the same row of windows) may be 5 cm or less, 3 cm or less, or may be around 1 cm. The length of the section of the catheter between proximal windows 18 and distal windows 16, which may be free of windows, may be 12 cm or less, 10 cm or less, or 8 cm or less. The windows 16, 18 may have a length of 6 mm or less, 5 mm or less, 4 mm or less, 3 mm or less, 2 mm or less, or 1 mm or less. In one embodiment, the windows may have a length that is less than the length of corresponding electrodes that are electrically exposed through the windows. It should be understood that the above catheter dimensions are exemplary only, and the catheter 10 may have dimensions that vary from the above ranges and specific measurements.

Figure 2:
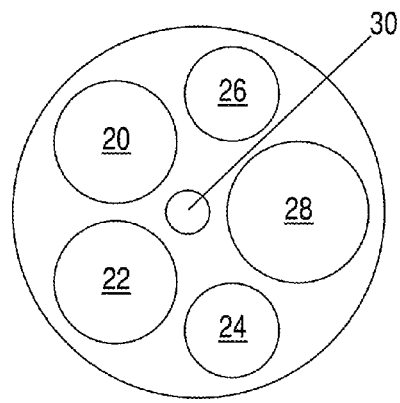
FIG. 2 is a cross-sectional view of the catheter shown in FIG. 1, showing lumen locations that may receive nerve-stimulating electrodes, according to an exemplary embodiment.

FIG. 2 illustrates a cross-sectional view along plane II-II (see FIG. 1A) of catheter 10. The interior of catheter 10 may include one or more lumens. In one embodiment, the catheter 10 may include six lumens 20, 22, 24, 26, 28, 30, although the catheter 10 may include fewer or more lumens. The lumens 20, 22, 24, and 26 may be electrode assembly lumens used to receive electrode assemblies described in further detail below. In one embodiment, proximal windows 18 may create a pathway between the interior of lumens 20, 22 and the exterior of catheter 10. Thus, lumens 20, 22 may receive electrodes that align with the proximal windows 18 shown in FIGS. 1A-1C. Similarly, distal windows 16 may create a pathway between the interior of lumens 24, 26 and the exterior of catheter 10, and lumens 24, 26 may receive electrodes that align with the distal windows 16 shown in FIGS. 1A-1C. Lumens 20, 22 may therefore be proximal electrode assembly lumens, and lumens 24, 26 may be distal electrode assembly lumens. As will be described in greater detail below, the proximal electrode assemblies placed in lumens 20, 22 may be used to stimulate a patient's left phrenic nerve, and the distal electrode assemblies placed in lumens 24, 26 may be used to stimulate a patient's right phrenic nerve. Lumen 28 may receive a guidewire, and lumen 30 may receive a steering mechanism, other instruments, wires, or may be used to transport fluid to or from a working site.

Figure 3A:
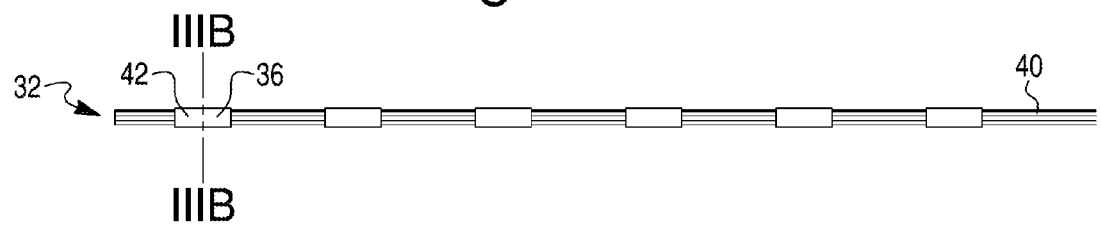
FIG. 3A illustrates an electrode assembly that may be applied for stimulating a left phrenic nerve.
Figure 3B:
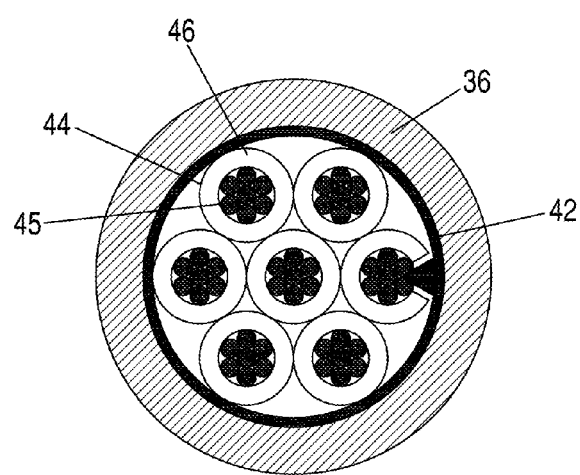
FIG. 3B illustrates a cross-sectional view of an electrode shown in FIG. 3A.
Figure 3C:
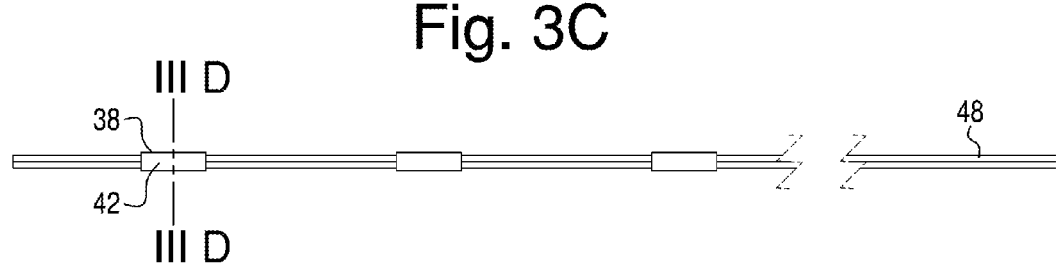
FIG. 3C illustrates an electrode assembly that may be applied for stimulating a right phrenic nerve.
Figure 3D:
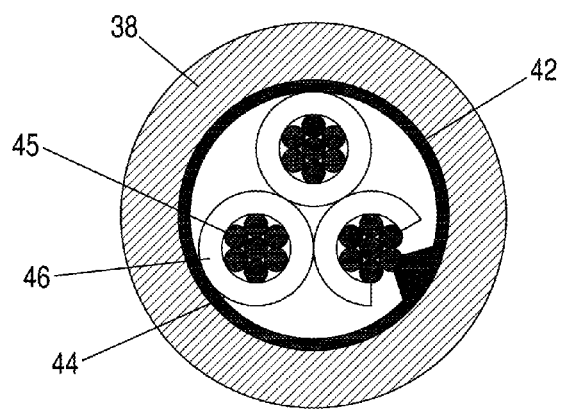
FIG. 3D illustrates a cross-sectional view of an electrode shown in FIG. 3C, according to exemplary embodiments.

FIG. 3A illustrates an exemplary embodiment of a proximal electrode assembly 32, and FIG. 3B illustrates a cross-sectional view of a single electrode 36 along plane IIIB-IIIB of FIG. 3A. In one embodiment, the proximal electrode assembly 32 may include six proximal electrodes 36. Similarly, FIG. 3C illustrates an exemplary embodiment of a distal electrode assembly 34, and FIG. 3D illustrates a cross-sectional view of a single electrode 38 along plate IIID-IIID of FIG. 3C. The distal electrode assembly 34 may include three distal electrodes 38. The two electrode assemblies 32 and 34 may differ from one another in terms of number of electrodes, structural features of the electrodes, and structural features of the assembly as a whole.

A proximal electrode assembly 32 may be held within one of proximal electrode assembly lumens 20, 22 of catheter 10, and a second proximal electrode assembly 32 may be held within the other of proximal electrode assembly lumens 20, 22 of catheter 10. Similarly, distal electrode assembly 34 may be held within one of distal electrode assembly lumens 24, 26 of catheter 10, and a second distal electrode assembly 34 may be held within the other of distal electrode assembly lumens 24, 26 of catheter 10. This combination of two proximal electrode assemblies 32 and two distal electrode assemblies 34 within the lumens of catheter 10 may allow the twelve proximal electrodes 36 to align with the twelve proximal windows 18 and the six distal electrodes 38 to align with the six distal windows 16.

FIGS. 3A and 3B will be referenced to describe proximal electrode assembly 32 in greater detail. Individual electrical leads 44 may be coiled together to form cable 40 of the proximal electrode assembly 32. Each lead 44 may include an elongated conductive member 45 and may be surrounded by a layer of non-conductive material 46. In one embodiment, the lead 44 may be a wire, the elongated conductive member 45 may include strands of stainless steel or another conductive material, and the non-conductive material 46 may be a layer of insulation. The leads 44 may deliver electrical or other signals to and from the electrodes 36.

In one embodiment, the cable 40 may include seven leads 44. Of these seven leads 44, six may be individually de-insulated at certain locations (e.g., underneath electrodes 36, as shown in FIG. 3B) to expose the conductive member 45 underneath. A conductive connector 42, which may be thin, flexible, and made of stainless steel or another conductive material, may be joined (e.g. mechanically, adhesive, micro-welded, etc.) to the exposed conductive member 45 and wrapped transversely around the cable 40. The conductive connector 42 may provide a contact surface between the exposed conductive member 45 and an electrode 36. In one embodiment, the electrode 36 may be a platinum-10% iridium (or any other suitable implantable electrode material like stainless steel, platinum, titanium nitride, coated stainless steel, etc.) ring electrode, which is crimped (or adhered, microwelded) to the exterior of the conductive connector 42 and cable 40. The seventh insulated lead 44 shown in the center of FIG. 3B may help support and stiffen the cable 40. The seventh lead 44 also may be used to carry other types of signals, for example signals from a sensor or ECG signals. In total, as noted above, two seven-lead proximal electrode assemblies may be inserted into the lumens 20, 22 of catheter 10.

Referring to FIGS. 3C and 3D, cable 48 of a distal electrode assembly 34 may include three electrical leads 44, which may be constructed in a similar manner as described in connection with the proximal electrode assembly 32. Three electrodes 38 may be mounted to conductive connectors 42, which are connected to exposed conductive members 45 of corresponding leads 44. In additional or alternative embodiments, partial or semi-circular electrodes may be used instead of ring electrodes 36, 38. The number of lumens within catheter 10, number of cables 40, 48, the number of electrodes 36, 38 on each cable 40, 48, respectively, and the distance between electrodes 36, 38, along with other structural features, may be varied to fit particular applications.

In one embodiment, any of the proximal electrodes 36 or the distal electrodes 38 may be used to measure electrical signals or other data from within the patient's body. In other words, in addition or alternatively to emitting or receiving electrical energy to produce a localized current for nerve stimulation, the electrodes may serve as sensors that receive electrical or other types of information from the patient.

Figure 4A:
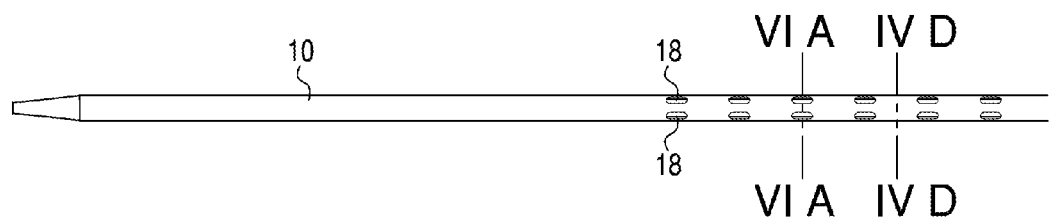
FIG. 4A illustrates a catheter.
Figure 4B:
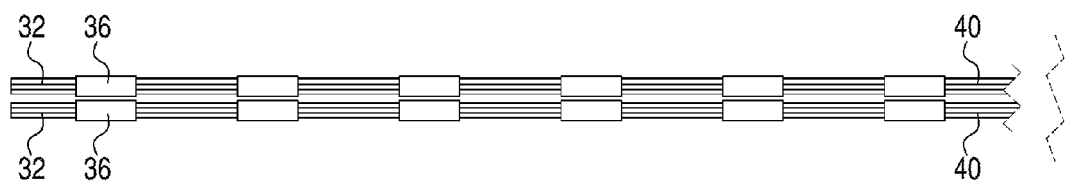
FIG. 4B illustrates an electrode assembly that may be positioned in the proximal end of the catheter of FIG. 4A and may be applied for stimulating a left phrenic nerve.
Figure 4C:
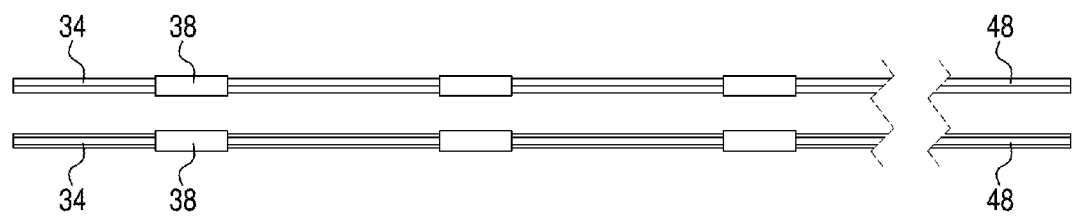
FIG. 4C illustrates an electrode assembly that may be positioned in the distal end of the catheter of FIG. 4A and may be applied for stimulating a right phrenic nerve.
Figure 4D:
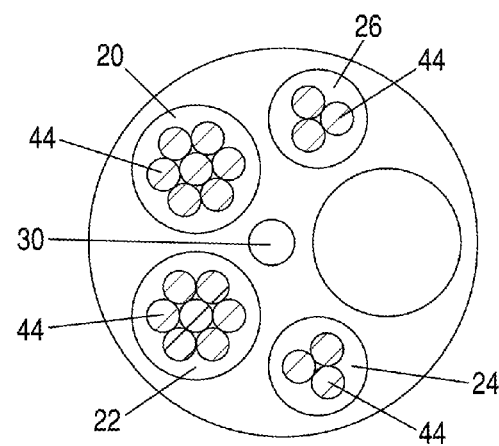
FIG. 4D illustrates a cross-sectional view of the catheter of FIG. 4A, with the electrode assemblies of FIGS. 4B and 4C shown within the lumens of the catheter, according to exemplary embodiments.

FIGS. 4A-4D illustrate how multiple electrode assemblies 32, 34 may be within the lumens of catheter 10. A catheter 10 is depicted in FIG. 4A, two proximal electrode assemblies 32 are depicted in FIG. 4B, and two distal electrode assemblies 34 are depicted in FIG. 4C. The two proximal electrode assemblies 32 may be placed within lumens 20, 22 of catheter 10 such that the electrodes 36 align with proximal windows 18. Similarly, the two distal electrode assemblies 34 may be placed within lumens 24, 26 of catheter 10 such that the electrodes 38 align with distal windows 16 (not shown in FIG. 4A). Once aligned, the electrode assemblies 32, 34 may be fixed (e.g. with adhesive or by any other structure or method) within their respective catheter lumens. FIG. 4D illustrates a cross-section of catheter 10, taken along plane IVD-IVD of FIG. 4A, that shows the catheter with two proximal electrode assemblies 32 and two distal electrode assemblies 34 within lumens 20, 22, 24, 26 of catheter 10.

Figure 5:
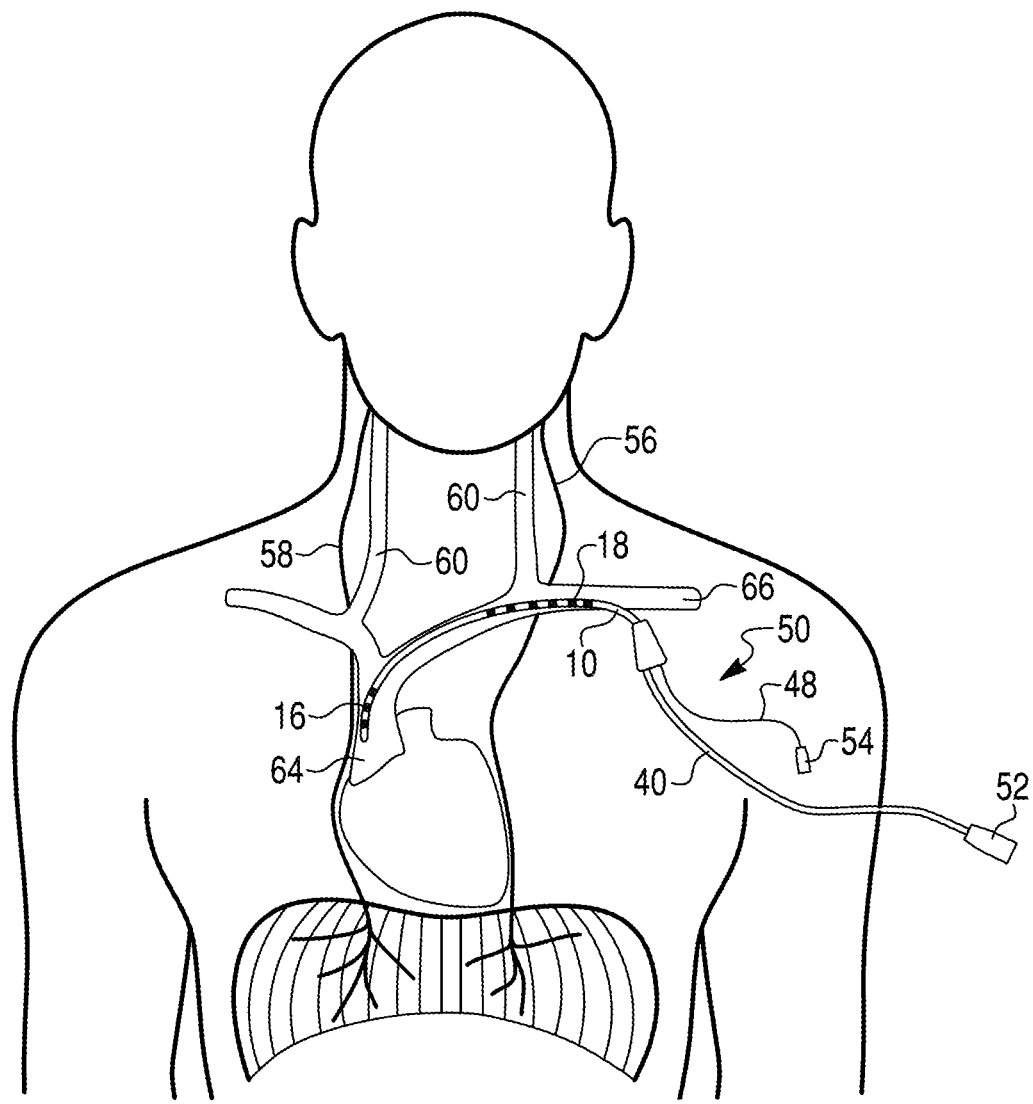
FIG. 5 illustrates the anatomy of selected nerves and blood vessels in a person's neck and upper torso.

Referring to FIG. 5, a medical device 50 may include a catheter 10 having two proximal electrode assemblies 32 and two distal electrode assemblies 34. The electrode assemblies 32, 34 may be within the elongated tubular member of catheter 10 such that electrodes 36 are exposed through proximal windows 18 and electrodes 38 are exposed through distal windows 16. The cables 40, 48 formed of electrical leads 44 may exit through the proximal end of the catheter 10 and may be attached (e.g. by solder, crimp, PCB, etc.) to connectors 52, 54.

To assemble medical device 50, the electrode assemblies 32, 34, which may include leads 44 and electrodes 36, 38, may be introduced into one or more lumens through lumen openings at either the proximal end or distal end of catheter 10. For example, the leads 44 may be inserted into a proximal end of the catheter 10 and threaded or pulled through one or more lumens until electrodes 36, 38 are located at predetermined locations in a more distal portion of the catheter 10. Portions of the catheter wall may be removed, either before or after insertion of the electrode assemblies 32, 34, to create windows 18, 16. Windows 18, 16 may expose the electrodes, allowing for a conductive path between the electrodes 36, 38 and the blood vessel lumen in which the medical device 50 may be placed.

Referring still to FIG. 5, in an exemplary method of use, the medical device 50 may be used for transvascular stimulation of nerves in the neck and/or chest of a human or other mammal (e.g., a pig, a chimpanzee). FIG. 5 illustrates the anatomy of selected nerves and blood vessels in the neck and chest of a human and, in particular, the relative locations of the left phrenic nerve (PhN) 56, right phrenic nerve 58, vagus nerves (VN) (not shown), external or internal jugular veins (JV) 60, brachiocephalic veins (BCV) 62, superior vena cava (SVC) 64, and left subclavian vein (LSV) 66.

The medical device 50 may be used to rhythmically activate the diaphragm by inserting the catheter 10, with one or more electrode assemblies 32, 34, percutaneously into central veins of a patient. Percutaneous insertion of the catheter 10 may be accomplished by the Seldinger technique, in which a guide wire is inserted through a hypodermic needle into a vein. The distal tip of the catheter is then passed over the guide wire and advanced into the vein. The shape and mechanical properties of the catheter may be designed to urge the catheter 10 to gently hug the vein wall in regions adjacent to the right and left phrenic nerves, as shown in FIG. 5.

In the embodiment of FIG. 5, the medical device 50 may be inserted into the left subclavian vein 66 and advanced into the superior vena cava 64. In another configuration, not shown, the medical device 50 may be inserted into the left jugular vein and advanced into the superior vena cava 64. The catheter 10 may be inserted in a minimally-invasive way and may be temporarily placed into, and thus removable from, the patient. In one embodiment, the windows 18 are oriented such that, when the catheter is inserted into the left subclavian vein 66, the six pairs of windows 18 are directed posteriorly towards the left phrenic nerve 56 and the three pairs of distal windows 16 are directed laterally towards the right phrenic nerve 58.

In one embodiment, the electrode assemblies 34 may include electrodes 38 arranged and oriented to most effectively stimulate a nerve extending parallel to the catheter 10 (e.g., the right phrenic nerve 58 in FIG. 5), and the electrode assemblies 32 may include electrodes 36 arranged and oriented to most effectively stimulate a nerve extending at transverse or right angles to the catheter 10 (e.g., the left phrenic nerve 56 in FIG. 5). In an additional or alternative embodiment, the electrode assemblies 34 may include electrodes 38 arranged and oriented to most effectively stimulate a nerve extending at transverse or right angles to the catheter 10, and the electrode assemblies 32 may include electrodes arranged and oriented to most effectively stimulate a nerve extending parallel to the catheter 10. In the embodiments described above, the electrodes 38 of the electrode assemblies 34 have been placed in a more distal location along catheter 10 than the electrodes 36 of electrode assemblies 32. However, in other embodiments, the electrode assemblies 32 may be arranged within the catheter 10 such that their electrodes 36 are more distal than the electrodes 38 of the electrode assemblies 34. In this alternative embodiment, the windows 16, 18 of the catheter 10 may be configured to accommodate the alternative placement of the electrode assemblies 32, 34.

Once the catheter is fully inserted into the patient, various pairs of bipolar electrode combinations can be tested to locate nerves of interest and to determine which electrodes most effectively stimulate the nerves of interest. For example, in one embodiment, testing may be done to locate the right phrenic nerve 58 and to determine which pair of electrodes 38 (out of the distal set of electrodes 38) most effectively stimulate the right phrenic nerve 58. Similarly, testing may be done to locate the left phrenic nerve 56 and to determine which pair of electrodes 36 (out of the proximal set of electrodes 36) most effectively stimulate the left phrenic nerve 56. As a non-limiting example, testing could involve the use of a signal generator to systematically send electrical impulses to selected electrodes. By observing the patient's condition or by using sensors, the ideal electrode pairs may be identified.

Figure 6A:
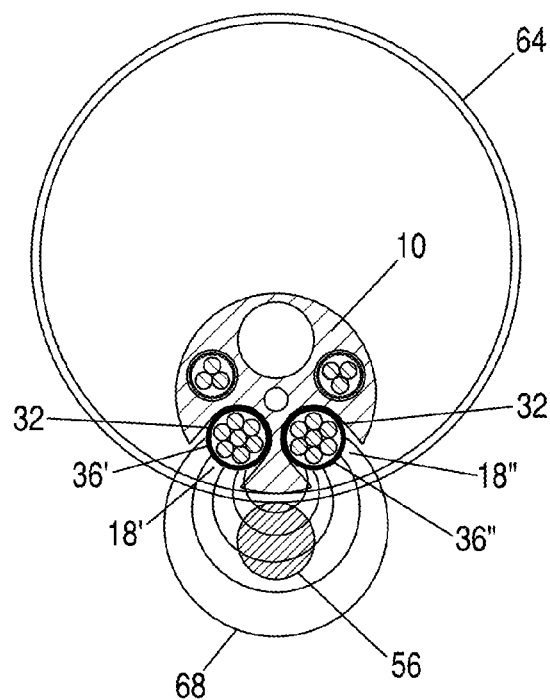
FIG. 6A illustrates electrical field lines produced by a catheter and electrode pair, according to an exemplary embodiment.

FIG. 6A illustrates a cross-sectional view of catheter 10 along the plane VIA-VIA shown in FIG. 4A and will be referenced to describe selective activation of a pair of electrodes for stimulating a nerve. The electrodes of FIG. 6A may be any electrode pair located at any location along catheter 10, and the nerve 56 may be any nerve located parallel, transverse, or at any other orientation with respect to catheter 10. However, for ease of description, proximal electrodes 36 and left phrenic nerve 56 are referenced in connection with FIG. 6A, even though left phrenic nerve 56 is shown transverse to catheter 10 in FIG. 5. Although not shown in FIG. 6A, a pair of distal electrodes 38 also may be selectively activated to stimulate the right phrenic nerve 58.

During "selective activation," an electrical potential may be created between a pair of selected bipolar electrodes, such as between a first electrode 36' and a second electrode 36". The first electrode 36' may be aligned with a first window 18', and the second electrode 36" may be aligned with a second window 18". The arrangement of the first and second electrodes 36', 36" and the first and second windows 18', 18" may create an electrical field 68 in the vicinity of first and second windows 18', 18". The first and second electrodes 36', 36" may be selected to effectively target a nerve, such as the left phrenic nerve 56 shown in FIG. 6A or another nerve near the electrodes 36', 36". The windows 18', 18" and the resulting electrical field 68 may therefore be oriented towards the left phrenic nerve 56 or other target nerve.

During nerve stimulation, electrical current flows from one of the electrodes 36', 36" to the other of the electrodes 36', 36", flowing through the windows 16', 16" and through the blood and surrounding tissues. The catheter 10 with windows 16', 16" therefore acts as an insulative barrier that constrains and focuses the electrical field 68, rather than allowing the electrical field 68 to expand radially outwards in all directions. The focused electrical field allows target nerve stimulation at lower energy levels and avoids stimulating unwanted nerves or other structures. In some embodiments, the stimulation current may be between 10-6000 nC (nanocoulombs) or between 50-500 nC.

Figure 6B:
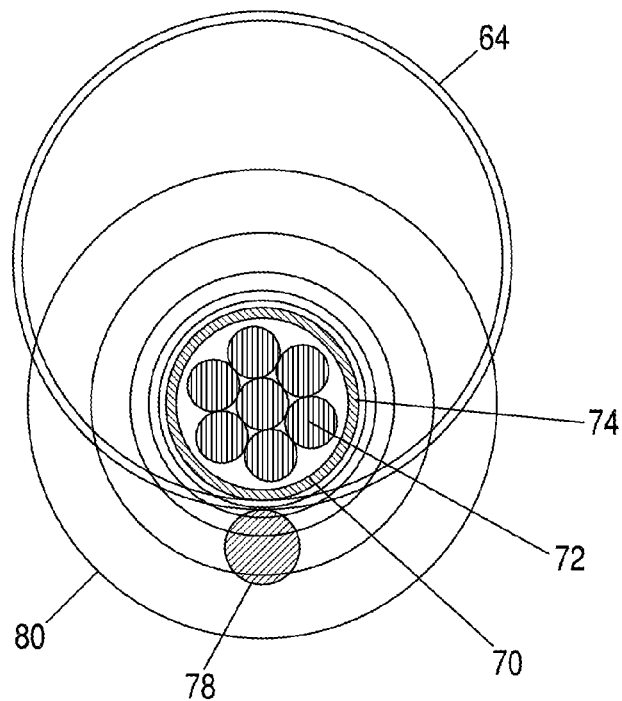
FIG. 6B illustrates the electrical field lines of an exemplary prior art electrode.

FIG. 6B illustrates an exemplary prior art nerve stimulation device 70 that may be used to stimulate a nerve 78. The prior art device 70 may include lead wires 72 and an electrode 74. The device 70 may be inserted into a blood vessel 76, and an electrical field 80 may be created around the device 70. As can be seen in FIG. 6B, the electrical field 80 may be created around the circumference of the device 70. Although it may target a nerve 78, the electrical field is not confined to a specific location and therefore may also target other anatomical structures within the patient. Thus, in general, the windows 16, 18 of catheter 10 may allow the use of lower and safer electrical currents to activate the phrenic nerves 56, 58 and prevent overstimulation or unwanted activation of nearby structures such as other nerves, muscles, or the heart.

Electrode Assembly Embodiments

FIGS. 7A-13K illustrate additional or alternative embodiments of electrodes and electrode assemblies that may be used with any of the catheters described herein. The below embodiments may be variations of the electrode assemblies and electrodes described previously. Therefore, features not mentioned may be unchanged or logical modifications of the above-described embodiments. For ease of reference, proximal electrodes 36, proximal electrode assemblies 32, distal electrodes 38, and distal electrode assemblies 34 of each embodiment will be referred to using the same reference numerals as used above, even though some features of these components may be modified in the below embodiments.

Bare/Sewn Wires

Figure 7A:
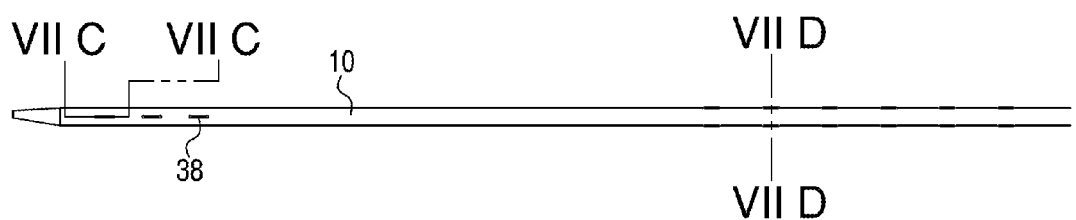
FIG. 7A illustrates a catheter having leads sewn into the catheter shaft.
Figure 7B:
FIG. 7B illustrates an electrode assembly that may be inserted into the catheter of FIG. 7A.
Figure 7C:
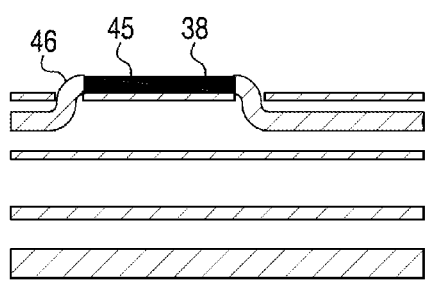
FIG. 7C illustrates a partial longitudinal cross section of a distal electrode of FIG. 7A.
Figure 7D:
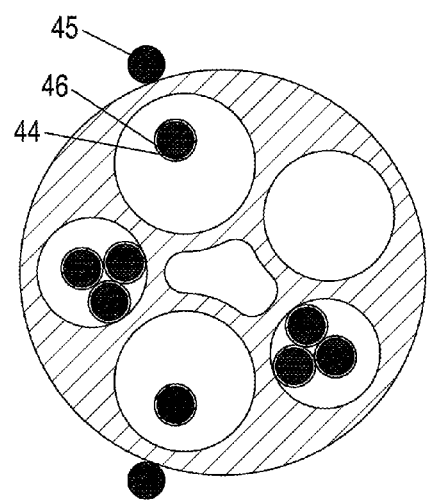
FIG. 7D illustrates a transverse cross-sectional view of a proximal electrode pair of FIG. 7A showing the inner lumens of the catheter, according to exemplary embodiments.

Referring to FIGS. 7A-7D, the layer of non-conductive material 46 may be removed from portions of leads 44 to expose the underlying conductive member 45. FIG. 7A illustrates a catheter 10, and FIG. 7B illustrates a proximal electrode assembly 32. The exposed conductive members 45 (straight or coiled for increased surface area) of leads 44 may be positioned within windows 16 or 18 of the catheter 10 and, in some embodiments, may extend radially out of the windows 16, 18. In another embodiment, as shown in FIG. 7C, the conductive member 45 may pass out of a lumen of the catheter 10 through an aperture in the catheter outer wall, travel in a proximal-distal direction, and then pass back through another aperture in the outer wall of catheter 10. The portion of the conductive member 45 that forms an electrode 36, 38 may be the distal end of a lead 44. The insulated leads 44 may additionally or alternatively be sewn into the catheter 10, leaving the exposed conductive member 45 on the exterior of the catheter 10 and the remaining insulated lead 44 inside a catheter lumen. FIG. 7D illustrates a cross-section of catheter 10 through a pair of proximal electrodes 36 that include exposed conductive members 45.

In some embodiments, a conductive member, such as an electrode described in connection with FIGS. 10A-10E, may be fixed (e.g., with adhesive, heat fusion, etc.) to the exterior of catheter 10 and in electrical contact (e.g., mechanically, microwelded) with the exposed conductive member 45. Fixing such a conductive member to the exposed conductive member 45 may increase certain electrical properties of the electrode, such as conductivity and surface area, relative to an electrode that only includes the exposed conductive member 45. Examples of conductive member material include platinum, platinum iridium, gold, stainless steel, titanium nitride, MP35N, palladium, etc.

Printed Electrodes

Figure 8A:
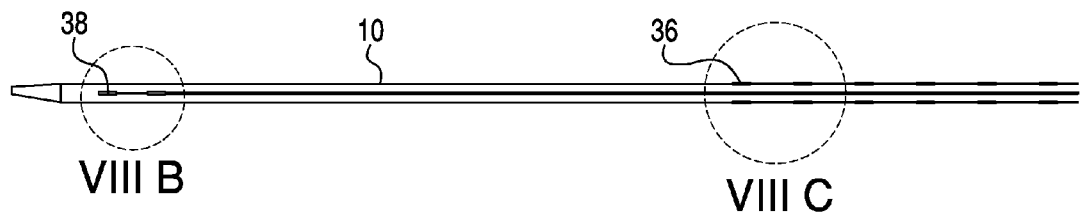
FIG. 8A illustrates a catheter having electrodes that are printed directly onto the exterior of the catheter.
Figure 8B:
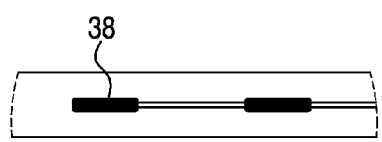
FIG. 8B illustrates an exploded view of distal electrodes of the catheter of FIG. 8A.
Figure 8C:
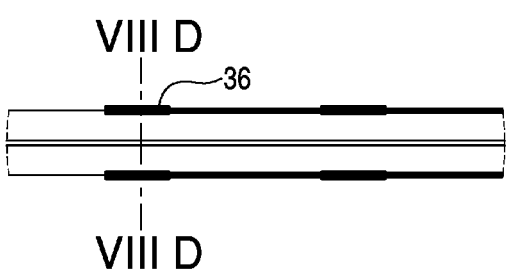
FIG. 8C illustrates an exploded view of proximal electrodes of the catheter of FIG. 8A.
Figure 8D:
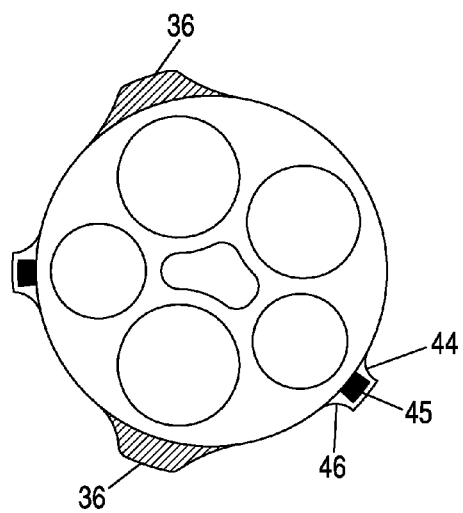
FIG. 8D illustrates a transverse cross-sectional view of an electrode pair of FIG. 8A, according to exemplary embodiments.
Figure 9A:
FIG. 9A illustrates a catheter.
Figure 9B:
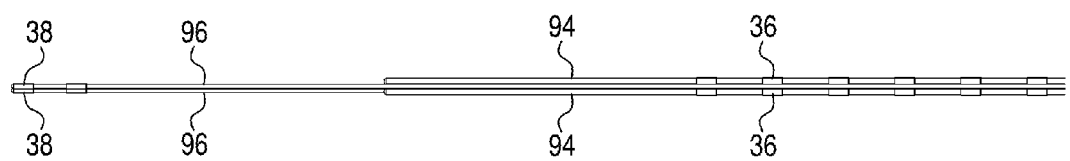
FIG. 9B illustrates proximal and distal electrode assemblies that may be inserted into lumens of the catheter of FIG. 9A.
Figure 9C:
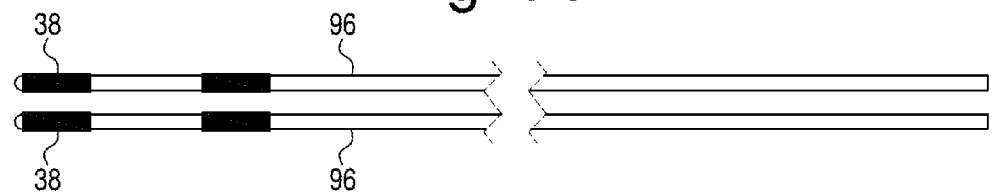
FIG. 9C illustrates an exploded view of the distal electrode assemblies shown in FIG. 9B.
Figure 9D:
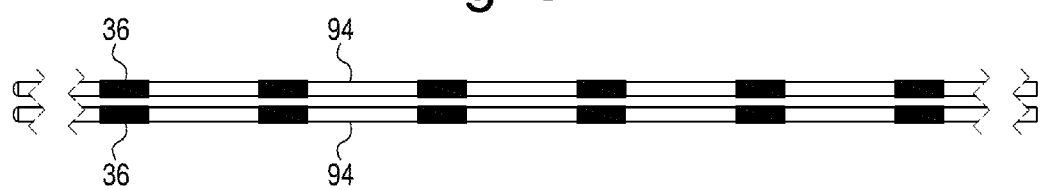
FIG. 9D illustrates an exploded view of the proximal electrode assemblies shown in FIG. 9B.
Figure 9E:
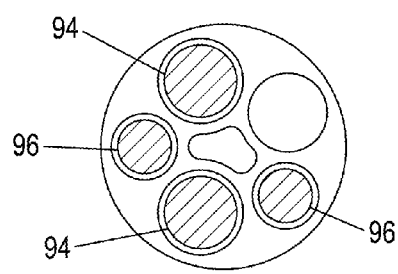
FIG. 9E illustrates a transverse cross-sectional view of the catheter of FIG. 9A, according to exemplary embodiments.
Figure 10A:
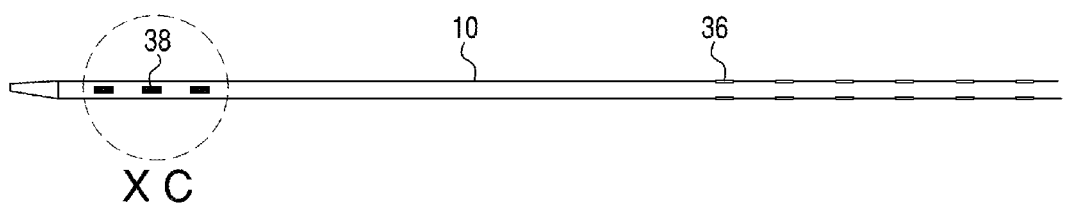
FIGS. 10A and 10B illustrate views of a catheter having electrodes that are adhered directly onto the exterior of the catheter.
Figure 10B:
Figure 10C:
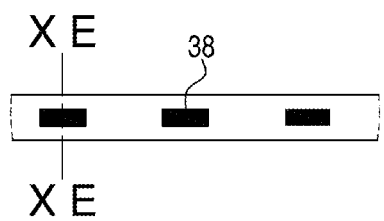
FIG. 10C illustrates an exploded view of electrodes shown in FIG. 10A.
Figure 10D:
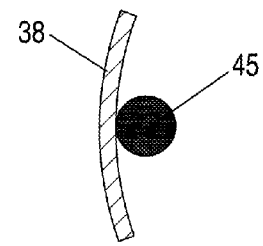
FIG. 10D illustrates a transverse, cross-sectional view of a single electrode.
Figure 10E:
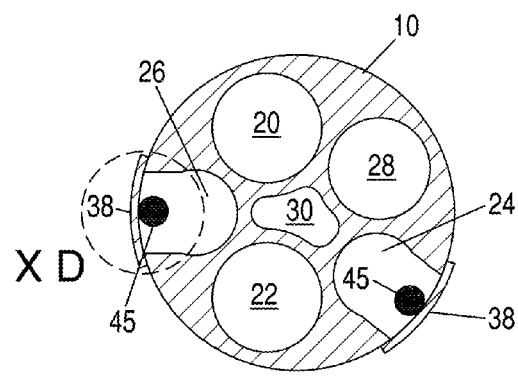
FIG. 10E illustrates a transverse, cross-sectional view of an electrode pair of FIG. 10A, according to exemplary embodiments.

FIG. 8A illustrates a catheter having electrodes and leads that are printed directly onto the exterior of catheter 10. FIG. 8B illustrates an exploded view of distal electrodes 38 of the catheter 10, FIG. 8C illustrates an exploded view of proximal electrodes 36 of catheter 10, and FIG. 8D illustrates a transverse cross-sectional view of a proximal electrode pair 36 taken along plane VIIID-VIIID of FIG. 8C. Electrodes 36, 38 may be formed by conductive inks (such as silver flakes or carbon flakes suspended in polymer). These conductive inks may be deposited and adhered directly onto the catheter 10 and sealed, except for the exposed electrodes 36, 38, with an outer polyurethane or other flexible insulative film. The exposed electrodes 36, 38 also may be coated (e.g., with titanium nitride) for purposes such as one or more of: enhancing electrical properties, such as conductivity and surface area; providing corrosion resistance; and reducing the potential for formation of silver oxide which could be toxic. As can be seen in FIG. 8C, the conductive ink trace of distal electrodes 38 may travel proximally along catheter 10 past the proximal electrodes 36.

The use of printed electrodes may reduce the overall complexity of the design while maximizing the useable catheter lumen space, without changing the catheter profile or flexibility too drastically. However, in some embodiments, the profile of the catheter may be reduced because of the space saved by using electrodes printed on the exterior of the catheter. In an additional or alternative embodiment, one or several catheter lumens may be used for fluid delivery, blood sampling, or central venous pressure monitoring. In another additional or alternative embodiment, several of the catheter lumens, such as lumens 20, 22, 24, 26 may be eliminated since there are no catheter assemblies as described in connection with other embodiments. Thus, in one embodiment, the catheter 10 may include only lumen 28 and lumen 30. If the catheter 10 with printed electrodes includes fewer than the six lumens shown in FIG. 2, for example, its cross-sectional area may be reduced, one or more of the fewer lumens may be made larger to accommodate larger tools or other objects, or one or more smaller lumens may be added to accommodate tools or other objects.

Electrode-Supporting Catheters

FIGS. 9A-9E illustrate electrodes 36, 38 supported by catheters 94, 96 that may be placed within a lumen of catheter 10. In this embodiment, proximal electrodes 36 may be joined by an electrode catheter 94, and distal electrodes 38 may be joined by an electrode catheter 96. The catheters 94, 96 may be elongated tubular members that include a non-conductive material. The electrodes 36, 38 may be crimped onto the catheters 94, 96 and may be electrically connected to conductive members 45 of leads 44 through the walls of the electrode catheters 94, 96. The catheters 94, 96 may have cross-sectional areas that are smaller than the cross-sectional areas of their respective lumens of catheter 10 so that catheters 94, 96 may be inserted into the lumens of catheter 10. When catheters 94, 96 are inserted into catheter 10, the electrodes 36, 38 may be aligned with windows 18, 16 of catheter 10 and fixed in place, similar to other embodiments. Although not shown in FIG. 9E, leads 44 may travel in a proximal-distal direction through the electrode catheters 94, 96.

In an additional or alternative embodiment, one or more catheters having a single electrode 36 or 38, or a pair of bipolar electrodes, may be inserted into a lumen of catheter 10 during a procedure (i.e., while catheter 10 is within a patient's vascular system) and advanced to various windows 18, 16 until optimal locations are found. By doing so, less material may be used, which may drive down the cost of production of the medical device 50.

Exterior Electrodes

FIGS. 10A-10E illustrate electrodes 36, 38 on the exterior of a catheter 10. In the embodiment of FIGS. 10A-10E, electrodes 36, 38 may be connected (microwelded, etc.) to a lead 44 and may be fixed (e.g., crimped, adhered, etc.) onto the exterior of catheter 10. The lead 44 may be inserted through the wall of the catheter 10 (e.g., through a window 16, 18) and into a lumen within the catheter 10.

In other embodiments, one or more ring electrodes may be fixed to the exterior of the catheter 10. To facilitate directional targeting of one or more nerves, an insulative coating may be applied to cover a portion of the electrodes.

Injection Molding

FIGS. 11A-11F illustrate an embodiment in which the manufacturing process of electrode assemblies 32, 34 may include injection molding. To obtain the electrode configuration shown in FIGS. 11B and 11C, electrodes 36, 38 may be individually attached to leads 44 by injection molding, with the electrodes 36, 38 in electrical contact with conductive members 45. The molding process may form a covering 98 around each lead 44. The covering 98 may include a non-conductive material, such as plastic. The electrodes 36, 38 may be flat, semi-circular, or any other suitable shape. Similarly, the covering 98 may form any shape around the leads 44, such as the shape shown in FIG. 11F.

Figure 11A:
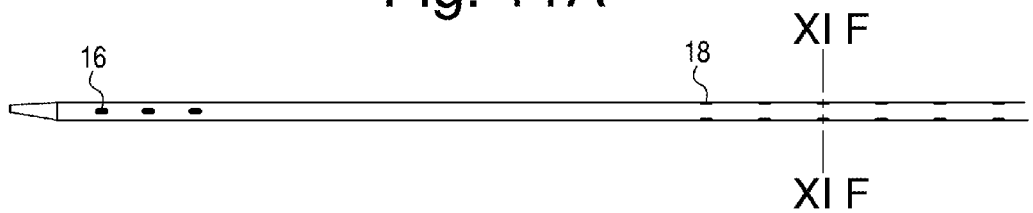
FIG. 11A illustrates a catheter.
Figure 11B:
FIG. 11B illustrates proximal and distal electrode assemblies held together by injection molding, according to a first exemplary embodiment.
Figure 11C:
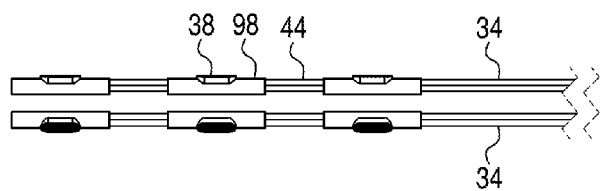
FIG. 11C illustrates an exploded view of the distal electrodes shown in FIG. 11B.
Figure 11D:
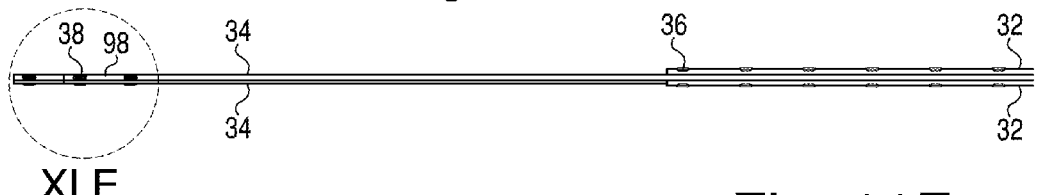
FIG. 11D illustrates electrode assemblies held together by injection molding, according to a second exemplary embodiment.
Figure 11E:
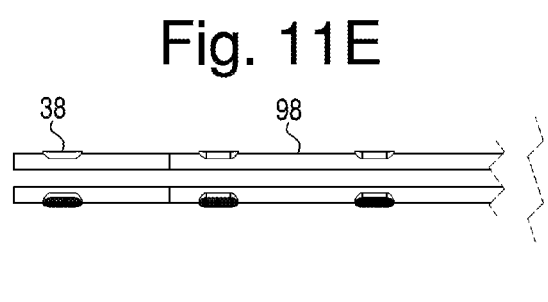
FIG. 11E illustrates an exploded view of the distal electrodes shown in FIG. 11D.
Figure 11F:
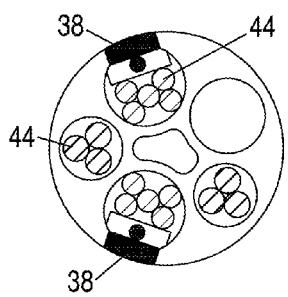
FIG. 11F illustrates a transverse, cross-sectional view of the catheter of FIG. 11A, showing the catheter lumens and electrode assemblies of FIG. 11B within the lumens.

In another embodiment, shown in FIGS. 11D and 11E, the electrodes 36, 38 and bundle of leads 44 may be placed within an injection molding jig that injects material, such as plastic, around the bundle of leads 44 to anchor the electrodes in place, forming a covering 98 but in one embodiment leaving at least a portion of the electrodes 38 exposed. In some embodiments, the electrodes may be covered by a thin layer of polymer, which may be removed in a subsequent step. In the embodiment of FIG. 11C, the covering 98 may be placed in the longitudinal vicinity of the electrodes and might only surround a single lead, and thus may be referred to as "partial." In the embodiment of FIG. 11E, the covering 98 may cover a larger longitudinal portion of the underlying leads 44 and may surround multiple leads, and thus may be referred to as "full." Once each electrode 38 is anchored to the leads 44, the electrode assemblies 32, 34 may be inserted into the lumens of catheter 10 and aligned with windows 18, 16.

Electrodes Supported by Tubular Members

FIGS. 12A-12K illustrate yet another embodiment of electrode assemblies 32, 34. In this embodiment, tubular members 100 may support the distal ends 102 of leads 44 and hold the distal ends 102 adjacent to electrodes 36, 38.

Figure 12F:
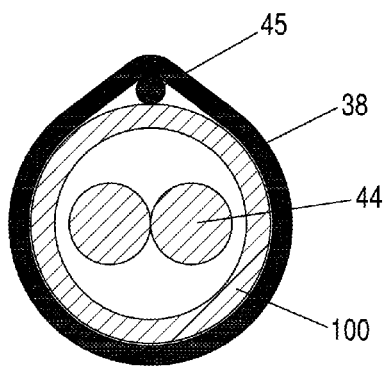
FIG. 12F illustrates a transverse cross-sectional view of a distal electrode of FIG. 12D.
Figure 12G:
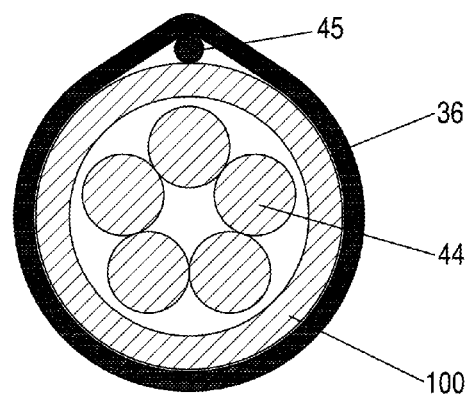
FIG. 12G illustrates a transverse cross-sectional view of a proximal electrode of FIG. 12E; 12H illustrates a transverse cross-sectional view of the catheter of FIG. 12A with two distal electrode assemblies of FIG. 12B within the catheter lumens.

FIG. 12A illustrates a catheter 10; FIG. 12B illustrates a perspective view of a distal electrode assembly 34; FIG. 12C illustrates a perspective view of a proximal electrode assembly 32; FIG. 12D illustrates a side view of the distal electrode assembly 34 of FIG. 12B; FIG. 12E illustrates a side view of the proximal electrode assembly 32 of FIG. 12C; FIG. 12F illustrates a transverse cross-sectional view of a distal electrode 38 of FIG. 12D; FIG. 12G illustrates a transverse cross-sectional view of a proximal electrode 36 of FIG. 12E; 12H illustrates a transverse cross-sectional view of the catheter of FIG. 12A with two distal electrode assemblies 34 of FIG. 12B within the catheter lumens; FIG. 12I illustrates a transverse cross-sectional view of the catheter 10 of FIG. 12A with two proximal electrode assemblies 32 of FIG. 12C within the catheter lumens; FIG. 12J illustrates the view of FIG. 12H with ECG wires through a central lumen of the catheter 10; and FIG. 12K illustrates the view of FIG. 12I with ECG wires through a central lumen of catheter 10.

FIGS. 12B-12G illustrate the proximal and distal electrodes 36, 38 of the proximal and distal electrode assemblies 32, 34, respectively. As can be seen in the figures, electrode assemblies 32, 34 include leads 44, similar to other embodiments. As shown most clearly in FIGS. 12F and 12G, the distal portions 102 of leads 44 may include exposed conductive members 45 and may be attached by welding or any other method to the exterior of a tubular member 100 and to the interior of electrodes 36, 38. The tubular member 100 may be 1-6 mm in length, 2-4 mm in length, and in one embodiment about 3 mm in length, although the tubular member 100 may be any other suitable length. The tubular member 100 may be a stainless steel hypodermic tube. (In FIGS. 12B-12E, tubular members 100 are not shown and would be all or mostly covered by electrodes 36, 38. Distal portions 102 of leads 44 are labeled in FIGS. 12D and 12E to show their general location, although they are underneath electrodes 36, 38.) As can also be seen in FIGS. 12F and 12G, the distal portions 102 of leads 44 may cause the electrodes 36, 38 to protrude radially outward.

Each lead 44 may travel proximally through any electrodes 38, 36 that are positioned more proximally than the electrode to which the distal end 102 of that lead is attached. For example, referring to FIG. 12B, the lead 44 that is attached to the most distal electrode 38 of the distal electrode assembly 34 may travel proximally through the other two electrodes 38 and through all six proximal electrodes 36. Referring to FIG. 12C, the lead 44 attached to the most distal electrode 36 may travel proximally through each of the other five electrodes 36.

In one embodiment, the distal electrode assembly 34 may include three leads 44—one for each electrode 38. Similarly, the proximal electrode assembly 32 may include six leads 44—one for each electrode 36. As the leads 44 of each electrode assembly 32, 34 join together, the leads may be coiled to form cables 48, 40. At more distal locations, cable 48 (formed of leads 44 from distal electrode assembly 34), may include one or two leads. At more proximal locations, such as proximal to the most proximal electrode 38, cable 48 may include three leads 44. Similarly, at more distal locations, cable 40 (formed of leads from proximal electrode assembly 32), may include one, two, three, four, or five leads. At more proximal locations, such as proximal to the most proximal electrode 36, cable 40 may include six leads 44.

Figure 12H:
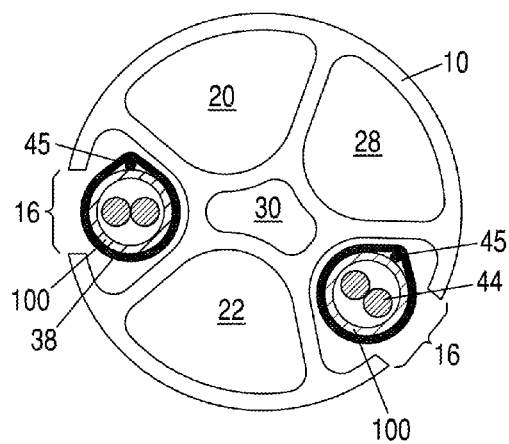
FIG. 12A illustrates a catheter.
FIG. 12B illustrates a perspective view of a distal electrode assembly.
FIG. 12C illustrates a perspective view of a proximal electrode assembly.
FIG. 12D illustrates a side view of the distal electrode assembly of FIG. 12B.
FIG. 12E illustrates a side view of the proximal electrode assembly of FIG. 12C.
FIG. 12I illustrates a transverse cross-sectional view of the catheter of FIG. 12A with two proximal electrode assemblies of FIG. 12C within the catheter lumens.
FIG. 12J illustrates the view of FIG. 12H with ECG wires through a central lumen of the catheter.
FIG. 12K illustrates the view of FIG. 12I with ECG wires through a central lumen, according to exemplary embodiments.
Figure 12I:
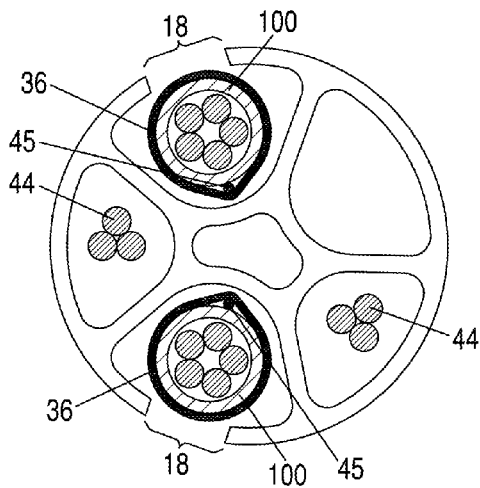
Figure 12J:
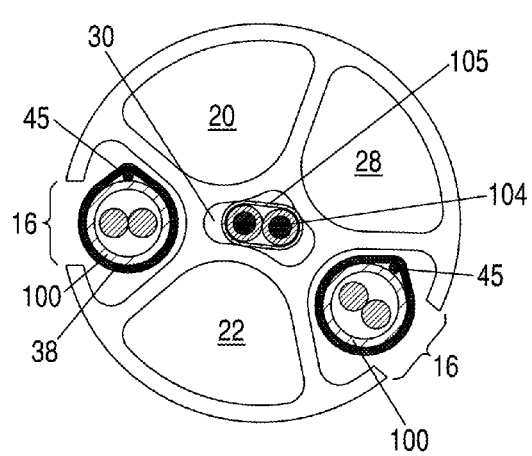
Figure 12K:
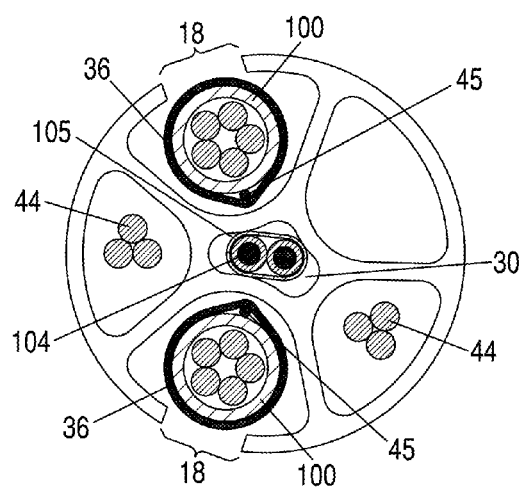

FIGS. 12H and 12I illustrate cross-sectional views with the electrode assemblies 34, 32 within lumens of the catheter 10. Although the lumens of catheter 10 illustrated in FIGS. 12H and 12I may be shaped differently than in FIG. 2, the catheter 10 may still include lumens 20, 22 configured to receive proximal electrode assemblies 32, lumens 24, 26 configured to receive distal electrode assemblies 34, a lumen 28 configured to receive a guidewire, and a lumen 30 configured to receive a steering mechanism or other structures. As can be seen in FIG. 12H, distal electrodes 38 may be aligned with distal windows 16. FIG. 12I illustrates proximal electrodes 36 aligned with proximal windows 18. The leads 44 from distal electrode assemblies 34 can be seen in the cross-sectional view of FIG. 12I because the leads 44 may travel proximally through lumens 24, 26.

FIGS. 12J and 12K are similar to the views shown in FIGS. 12H and 12I, except FIGS. 12J and 12K illustrate two electrocardiography (ECG) conductive members 104 within lumen 30. ECG conductive members 104 may be coupled to one or more ECG electrodes 106 (see FIG. 12A and FIG. 14) located at a distal end of catheter 10, for sensing ECG signals of a patient.

One benefit of the embodiments of FIGS. 12A-12K is that each electrode 36, 38 may be movable with respect to other electrodes 36, 38. Although the electrodes 36, 38 are connected by leads 44, the leads 44 typically are flexible. Therefore, when placing electrode assemblies 32, 34 within catheter 10 during manufacture of the medical device 50, this embodiment allows each electrode 36, 38 to be positioned within its respective window 18, 16 at least partially independently of other electrodes. Independent positioning of the electrodes may allow positioning errors to be minimized, as opposed to embodiments in which electrodes 36, 38 are fixed to other electrodes by a catheter or other rigid structure.

Arcuate Electrodes

FIGS. 13A-13K illustrate an embodiment that is similar to the embodiment shown in FIGS. 12A-12K. Similar features from the embodiment of FIGS. 12A-12K will not be repeated here. The main difference between the embodiment of FIGS. 13A-13K and the embodiment of FIGS. 12A-12K is that each of the electrodes 36, 38 of FIGS. 13A-13K may form an arcuate shape that functions to hold and contact the distal ends 102 (including exposed conductive members 45) of leads 44. The proximal and distal assemblies 32, 34 of FIGS. 13A-13K may or may not include tubular members 100.

Figure 13A:
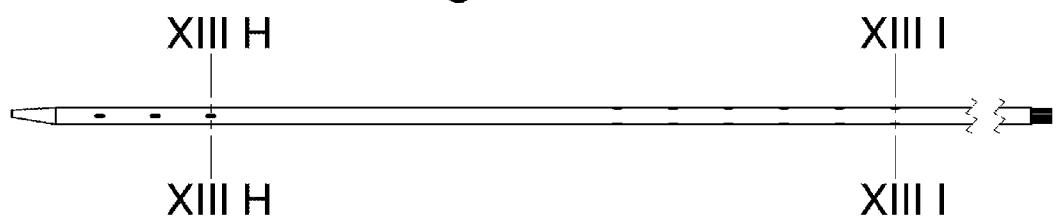
FIG. 13A illustrates a catheter.
Figure 13B:
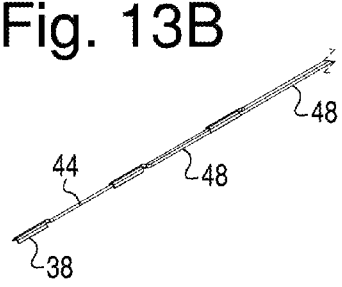
FIG. 13B illustrates a perspective view of a distal electrode assembly having arcuate electrodes.
Figure 13C:
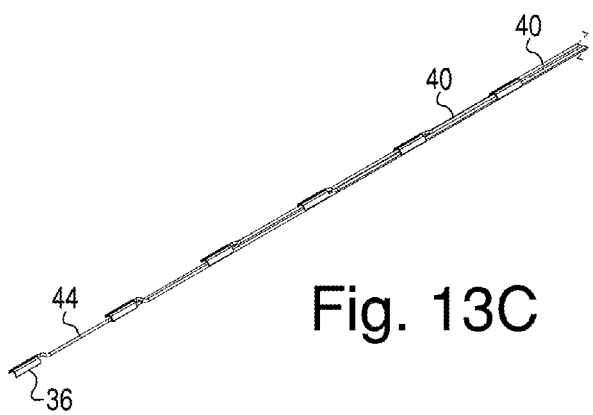
FIG. 13C illustrates a perspective view of a proximal electrode assembly having arcuate electrodes.
Figure 13D:
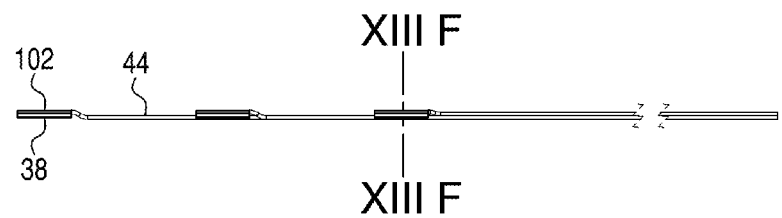
FIG. 13D illustrates a side view of the distal electrode assembly of FIG. 13B.
Figure 13E:
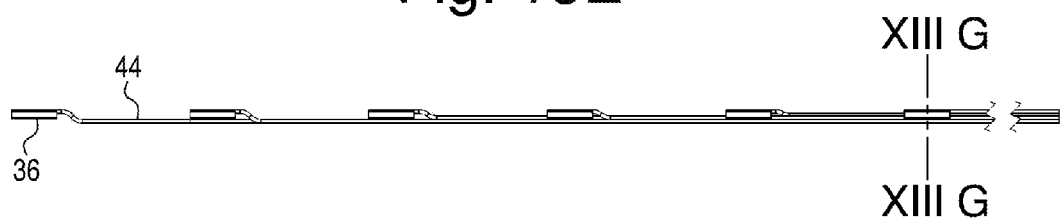
FIG. 13E illustrates a side view of the proximal electrode assembly of FIG. 13C.
Figure 13F:
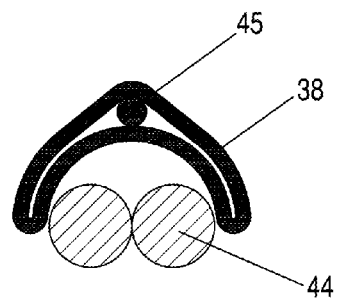
FIG. 13F illustrates a transverse cross-sectional view of a distal electrode of FIG. 13D.
Figure 13G:
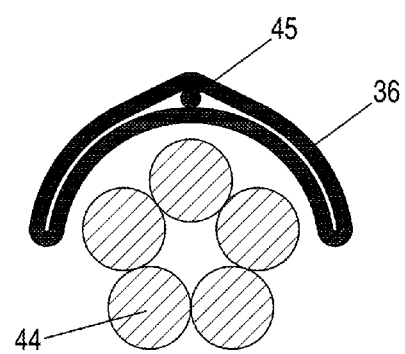
FIG. 13G illustrates a transverse cross-sectional view of a proximal electrode of FIG. 13E; 13H illustrates a transverse cross-sectional view of the catheter of FIG. 13A with two distal electrode assemblies of FIG. 13B within the catheter lumens.
Figure 13H:
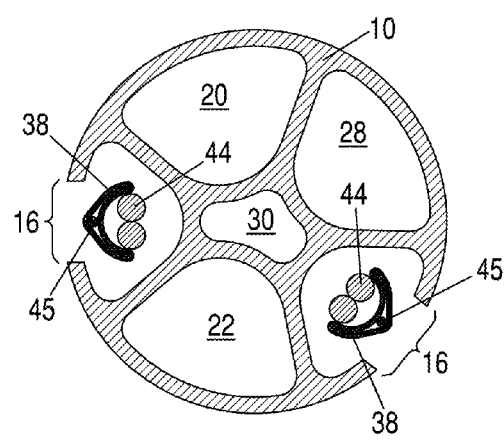
FIG. 13I illustrates a transverse cross-sectional view of the catheter of FIG. 13A with two proximal electrode assemblies of FIG. 13C within the catheter lumens.
FIG. 13J illustrates the view of FIG. 13H with ECG wires through a central lumen of the catheter.
FIG. 13K illustrates the view of FIG. 13I with ECG wires through a central lumen, according to exemplary embodiments.
Figure 13I:
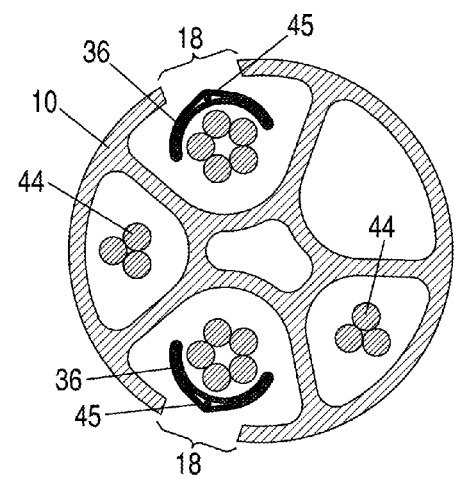
Figure 13J:
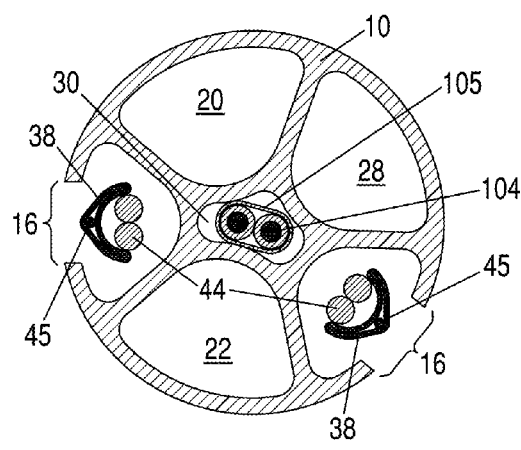
Figure 13K:
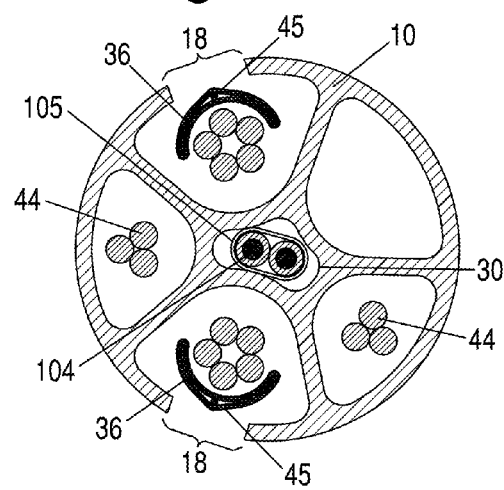

As shown in FIGS. 13F and 13G, each of the electrodes 36, 38 may be C-shaped and may have an outer wall 108 and an inner wall 110. The outer wall 108 and the inner wall 110 of an electrode may sandwich the exposed conductive member 45 at the distal end 102 of a lead 44.

Electrocardiography Electrodes

Figure 14:
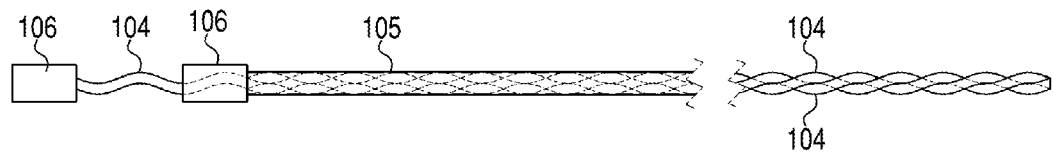
FIG. 14 illustrates individually shielded ECG wires, according to an exemplary embodiment.

FIG. 14 illustrates two ECG electrodes 106 and their associated components. As with all other features in this application, the ECG electrodes 106 may be used with any of the other embodiments described herein. The ECG electrodes 106 may be located at a distal end of a catheter 10 (see FIG. 12A). In one embodiment, the catheter 10 may include two ECG electrodes 106, although in some embodiments the catheter 10 may include one electrode 106 or more than two electrodes 106. A conductive member 104, which may be insulated, may connect each electrode 106 to an ECG system located outside of the patient. The ECG conductive members 104 may be braided or twisted together and may be surrounded by a non-conductive layer 105 (also shown in FIGS. 12J and 12K).

The electrodes 106 may monitor a patient's heart rate. Heart rate monitoring may be beneficial during use of medical device 50 to alert a medical practitioner to changes in the patient's heart rate. Changes in the patient's heart rate may be caused by the medical device 50 stimulating certain nerves or by unintentional stimulation of the patient's heart. Heart rate monitoring also may be relied on to achieve steady recruitment of a nerve. For example, the catheter 10 may move when a patient's heart beats, causing fluctuations in nerve stimulation. If the patient's heart rate is known, the electrical potential created between a pair of bipolar nerve-stimulating electrodes can be adjusted in real time to deliver a constant charge to the nerve.

Steering Mechanisms

A variety of steering mechanism may be included in a medical device 50 to help control positioning of catheter windows 16, 18, and thus electrodes 38, 36, within a blood vessel. A steering mechanism may be located within a central lumen 30 of catheter 10 or within other lumens of the catheter 10. It may be beneficial to position at least some electrodes 36, 38 in close proximity to each target nerve, as having electrodes situated close to the nerve can reduce the amount of current shunted through the blood and thus may reduce the electrical current needed to activate the nerve.

Several factors may help position the proximal windows 18 in a desired location within a blood vessel. For example, the typical subclavian vein penetration angle and the shape and elasticity of catheter 10 may combine to position the proximal windows 18 along a posterior wall of the subclavian vein, in close proximity to the left phrenic nerve, which normally descends dorsal to the left subclavian vein.

To ensure that the distal portion of the catheter 10, including windows 16 and their associated electrodes 38, is positioned in a desired location with respect to the right phrenic nerve, the medical device 50 may include stiffening elements and steering mechanisms. In one embodiment, the stiffening elements and steering mechanisms may help position the distal set of electrodes 38 against a lateral wall of the superior vena cava, close to the right phrenic nerve.

Turn Member Steering Mechanism

Figure 15A:
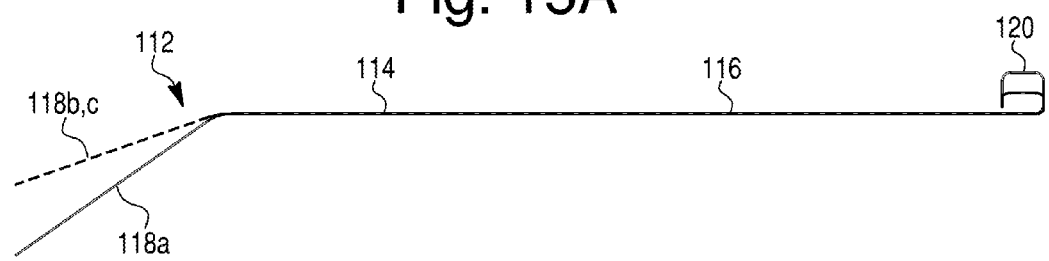
FIGS. 15A, 15B, and 15C illustrate various views of a steering mechanism for steering a distal catheter tip, according to an exemplary embodiment.
Figure 15B:
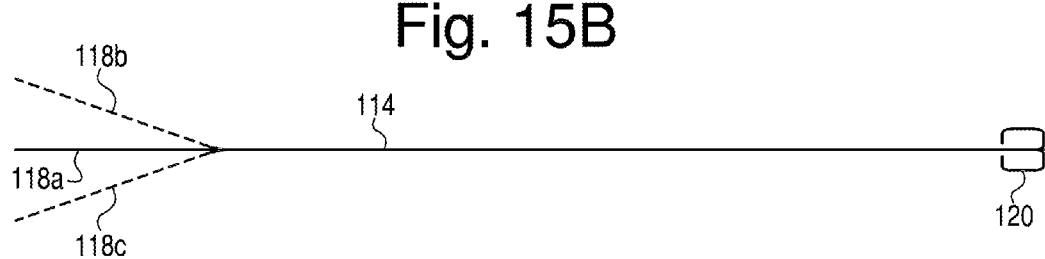
Figure 15C:
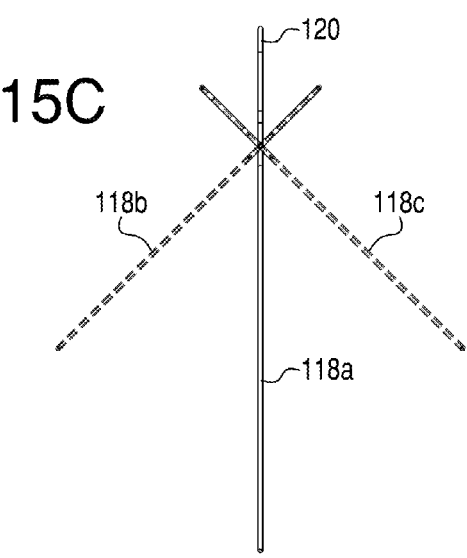

Referring to FIGS. 15A-15C, a steering mechanism 112 may include a single pre-shaped elongated member 114, such as a wire or tube (i.e. stainless steel, nitinol, hypodermic tube, etc.) to steer the catheter 10. The elongated member 114 may include a handle 120, a proximal portion 116 coupled to the handle 120, and a distal portion 118 that is bent with respect to the proximal portion 116. When the proximal portion 116 is turned via the handle 120, the distal portion 118 may correspondingly turn into a variety of positions and may function to position the distal end of catheter 10.

FIGS. 15A-15C illustrate the elongated member 114 in three different positions: a first position indicated by distal portion 118*a*, a second position indicated by distal portion 118*b*, and a third position indicated by distal portion 118*c*. FIG. 15A illustrates a front view of the steering mechanism 112 in three different positions, FIG. 15B illustrates a top view of steering mechanism 112 in three different positions, and FIG. 15C illustrates a view from the distal end of the steering mechanism 112 to the proximal end of the steering mechanism 112 when the steering mechanism 112 is in three different positions.

Elongated member 114 may be stiff enough to ensure that the distal portion of the catheter 10, which includes the distal electrodes 38, is placed against the vessel wall. The elongated member 114 also may be stiff enough to transmit steering torque from the proximal handle 120 to the distal portion 118.

Control Member Steering Mechanisms

Referring to FIGS. 16A-16E, another embodiment of steering mechanism 112 may include one or more control members 122. In one embodiment, the control members 122 may be pulled or pushed to bend or deflect a portion of catheter 10. The control members 122 may be surrounded by and may slide longitudinally relative to one or more tubular members 124, such as hypodermic tubes or compression coils. The tubular members 124 may be flexible. The steering mechanism 112 of this embodiment may further include a stiffening element 126, such as a tube or rod, which may be attached (e.g., by weld, adhesive, etc.) to the tubular members 124.

Figure 16A:
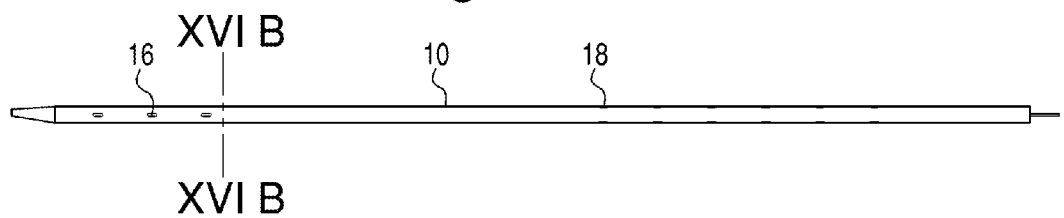
FIG. 16A illustrates a catheter having a steering mechanism that includes a stiffening element and two pull wires that are adhered within a central lumen of the catheter; FIG.
Figure 16B:
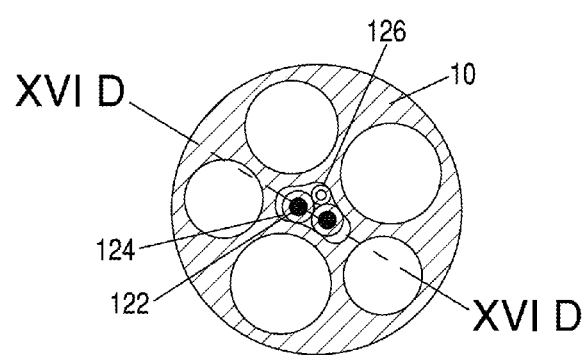
FIG. 16C illustrates a side view of the steering mechanism.
FIG. 16D illustrates a longitudinal cross-sectional view of the distal portion of the catheter of FIG. 16A showing an exploded view of the steering mechanism.
FIG. 16E illustrates an exploded view of a portion of the steering mechanism shown in FIG. 16D, according to exemplary embodiments.
Figure 16C:
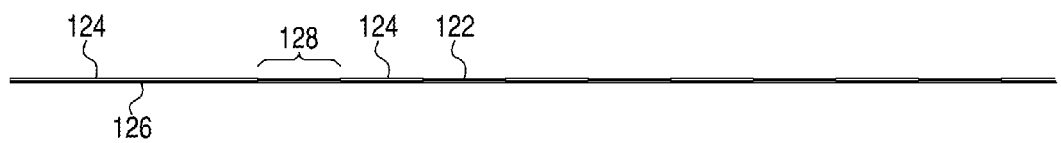
Figure 16D:
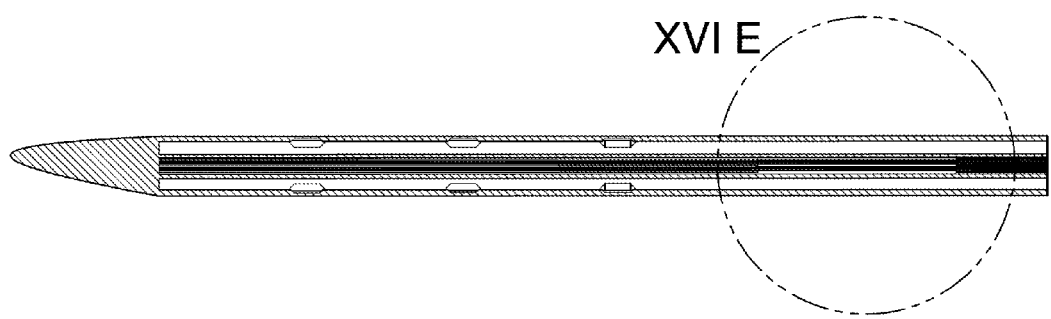
Figure 16E:
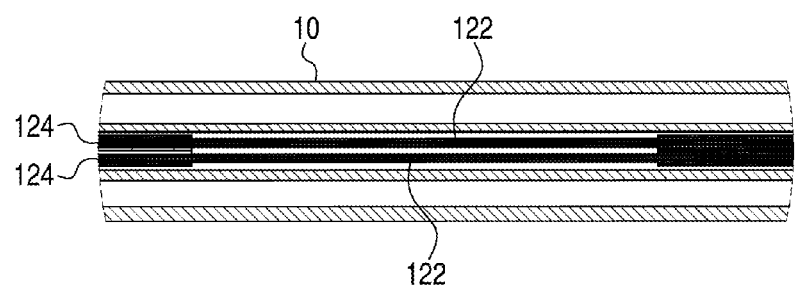

The embodiment of FIGS. 16A-16E may allow bidirectional steering of catheter 10. At a proximal end of the steering mechanism 112, a handle (not shown) may facilitate pulling or pushing of the control members 122 relative to their corresponding tubular members 124. As shown in FIG. 16C, the distal end of the steering assembly 112 may include gaps 128 between tubular members 124. The gaps 128 may facilitate bending of the distal end of the catheter 10. Once assembled, the steering mechanism 112 may be adhered within the central lumen 30 or another lumen of the catheter 10.

Figure 17A:
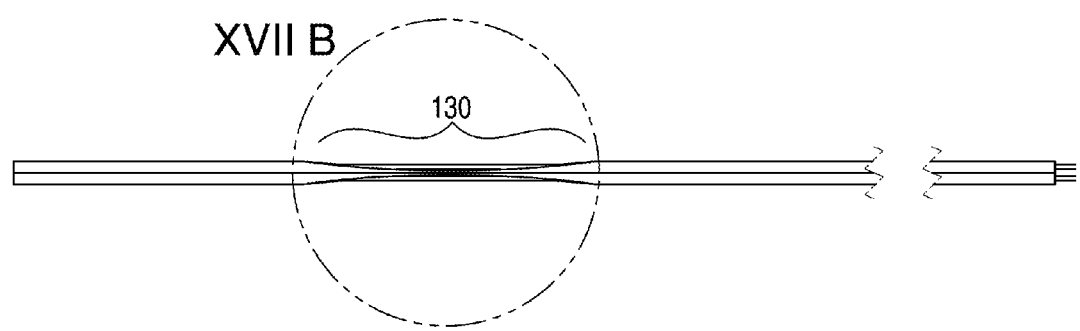
FIGS. 17A and 17B illustrate a steering mechanism that includes two hypodermic tubes with laser cut portions to help direct bending, according to an exemplary embodiment.
Figure 17B:
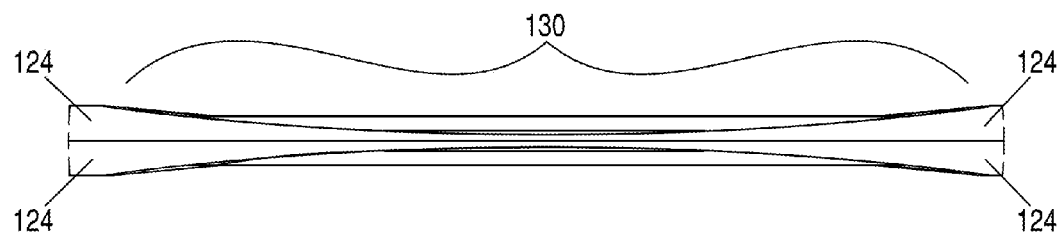
Figure 19D:
FIG. 19D illustrates a longitudinal cross-sectional view of the distal portion of the catheter of FIG. 19A showing the steering mechanism.
Figure 19E:
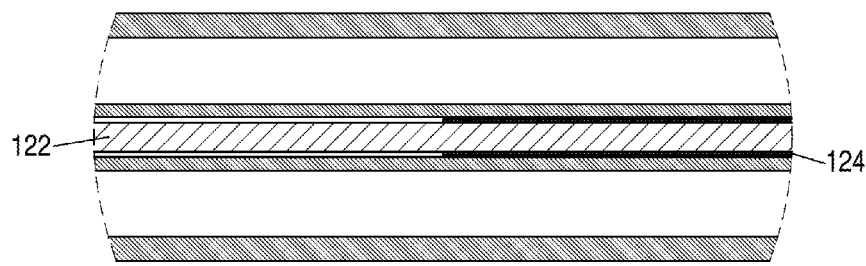
FIG. 19E illustrates an exploded view of a portion of the steering mechanism shown in FIG. 19D, according to exemplary embodiments.

Referring to FIGS. 17A and 17B, in an additional or alternative embodiment, tubular members 124 may include narrowed portions 130. The narrowed portions 130 may replace the gaps 128 or may be used in combination with gaps 128 to provide the desired flexibility. The narrowed portions 130 may be formed using a laser or by any other method.

Referring to FIGS. 18A-18E, in yet another embodiment of steering mechanism 112, control members 122 may be located in separate lumens 132, 134 within catheter 10. Similar to the embodiment of FIGS. 16A-16E, the control members 122 may be surrounded by one or more tubular members 124, which may be hypodermic tubes or compression coils. In one embodiment, each tubular member 124 does not surround a distal end portion of its respective control member 122. The distal end portion of the control member 122 may therefore be fixed to the distal end of its corresponding lumen 132, 134. A distal end portion of each tubular member 124 also may be fixed to its respective lumen 132, 134 at a position more proximal than the fixed portion of the control member 122. A gap extending longitudinally along the lumen may be left between the fixed portion of the control member 122 and the fixed portion of its corresponding tubular member 124 such that, when the control member 122 is pulled or pushed relative to its tubular member 124, deflection of the catheter 10 occurs within the gapped space.

In yet another embodiment, referring to FIGS. 19A-19E, steering mechanism 112 may include a single control member 122. The control member 122 may be surrounded by a tubular member 124 and may be pushed or pulled relative to the tubular member 124 to deflect the distal end of catheter 10. A distal portion of the control member 122 may be fixed within the distal end of lumen 30, or another lumen of catheter 10, and the tubular member 124 may be fixed to a more proximal location within lumen 30. Again, a gap may be formed between the fixed portion of control member 122 and the fixed portion of tubular member 124 to control the deflection locations of the catheter 10. In one embodiment, the control member 122 may be pulled to deflect the catheter tip in one direction and pushed to deflect the catheter tip in the other, opposite direction.

In some embodiments, any of the steering mechanisms described above may include a balloon, which may be inflated to assist in urging the distal portion of the catheter 10 and the distal electrodes 38 against the superior vena cava lateral wall. The balloon may be attached to a side of the catheter opposite the windows corresponding to distal electrodes 38. Upon inflation of the balloon, electrodes 38 may be urged towards a wall of the superior vena cava.

Catheter Embodiments

Catheter Window Arrangements

Figure 20A:
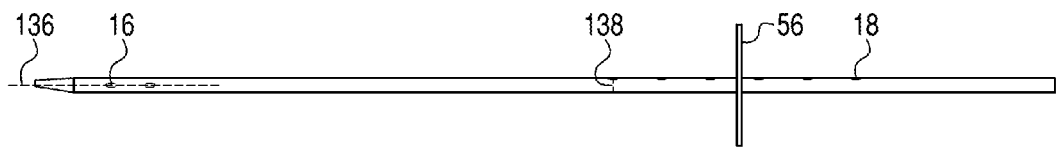
FIGS. 20A, 20B, and 20C illustrate catheters having different window alignments, according to exemplary embodiments.
Figure 20B:
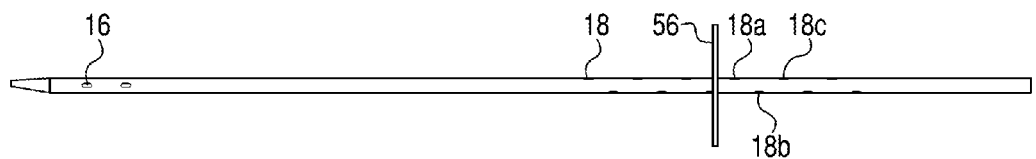
Figure 20C:
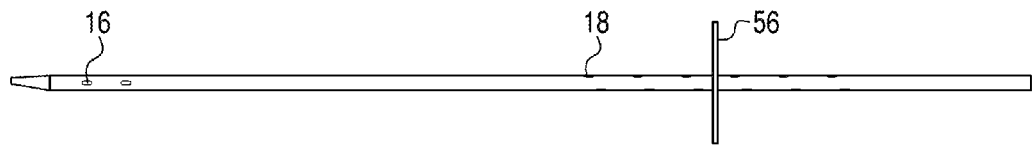

Referring to FIGS. 20A-20C, the windows 16, 18 of catheter 10 may have a variety of alternative configurations. For example, instead of being aligned as shown in FIG. 1, windows 16 may be offset from other windows 16, and windows 18 may be offset from other windows 18 with respect to a proximal-distal line 136 on the exterior surface of catheter 10 or with respect to a circumferential line 138 around the circumference of catheter 10. For example, windows 16 may be offset from each other if the more proximal window 16 does not lie on the same proximal-distal line 136 drawn through the center of the most distal window 16. Each window 18 of FIGS. 20B and 20C may be offset from other windows 18 with respect to circumferential lines 138 drawn through the center of windows 18. Embodiments of catheter 10 include windows 16, 18 with any configuration of offset and non-offset windows. As noted earlier, the set of windows 16 or rows of windows 16 may be offset from the set of windows 18 or rows of windows 18 with respect to a proximal-distal line 136.

In addition to electrode proximity to the nerves, electrode configuration relative to the nerve, as determined by windows 16, 18, may reduce the amount of electrical current required to stimulate nerve axons. Nerve axons may require lower activation currents when the electrodes and the direction of current flow are parallel to or along the nerve, thus producing a longitudinal transmembrane depolarization of sufficient magnitude to initiate action potentials. The direction the nerve courses is not exactly known and can vary from one individual to another.

Providing a plurality of different possible electrode configurations permits selection of sets of electrodes to be used for nerve stimulation in an individual. Using proximal electrodes 36 as an example, electrode pairs may be arranged in a straight line (e.g., along circumferential line 138 as in FIG. 20A), staggered (e.g., FIG. 20B), or angled (e.g., FIG. 20c) along a circumference of the catheter 10 to ensure that the nerves may be effectively stimulated. Referring to FIG. 20A, the circumferential line 138 may pass through (or over) the center of two electrodes, or the circumferential line 138 may pass through (or over) other portions of the two electrodes (e.g., the pair of electrodes may be slightly offset). Referring to FIG. 20B, staggered electrode pairs may be arranged such that the longitudinal distance (along a proximal-distal line parallel to the longitudinal axis of catheter 10) between longitudinally adjacent electrodes (such as between electrodes 18a and 18b), is approximately equal to the longitudinal distances between other pairs of longitudinally adjacent electrodes, such as 18b and 18c. Referring to FIG. 20C, angled pairs of electrodes may be arranged such that planes passing through the center of the pairs of electrodes do not form a right angle with respect to the longitudinal axis of the catheter 10. Thus, the staggered electrode embodiment of FIG. 20B is a subset of the angled electrode embodiment of FIG. 20C, and the embodiment of FIG. 20A in which a circumferential line 138 passes through or over non-center portions of electrode pairs also may be considered to include angled electrode pairs. The electrode configuration may be varied along the catheter 10 to account for the anatomical differences found among different patients. Selecting appropriate electrode pairs can provide effective nerve stimulation despite these differences.

Pre-Shaped Catheter

Figure 21:
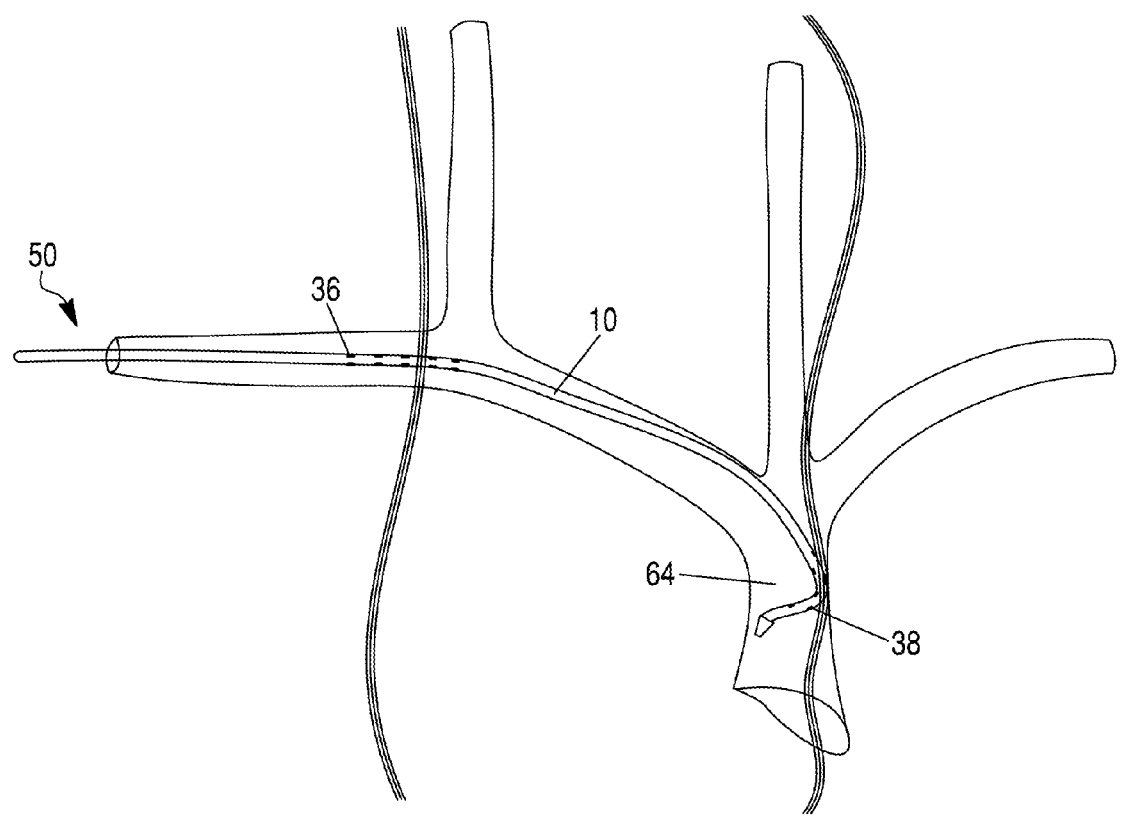
FIG. 21 illustrates a dorsal view of human blood vessels and left and right phrenic nerves, with a pre-shaped catheter inserted within the blood vessels, according to an exemplary embodiment.

FIG. 21 illustrates a medical device 50 having a pre-shaped catheter 10, with electrodes 36, 38 according to any embodiments disclosed herein. The pre-shaped catheter 10 may have arcuate, coiled, s-shaped, u-shaped, or any other pre-shaped portions. The pre-shaped catheter 10 may help ensure that the electrodes 36, 38 are in close contact with the vessel wall and thus closer to the phrenic nerve or other nerves, even in individuals where the right phrenic nerve may course more anteriorly or posteriorly than normal.

The pre-shaping of the catheter 10 may be accomplished, for example, by a stiffening element inserted within the catheter lumens, or pre-shaped during the manufacturing process. The pre-shaped catheter 10 may be flexible but may have some stiffness and may tend to return to its pre-shaped configuration. When inserted over a stiffer guidewire, the catheter 10 may straighten for the ease of insertion. When the guidewire is taken out, the catheter 10 may return to its pre-shaped form.

Catheter with Elongated Openings

Figure 22A:
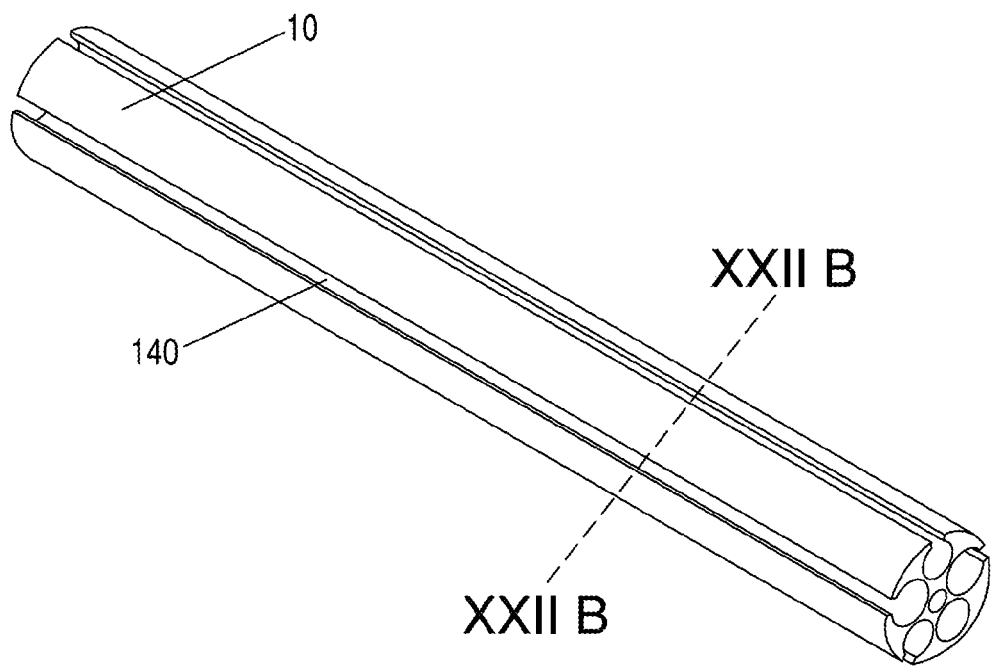
FIG. 22A illustrates a catheter having longitudinal slots along its length.
Figure 22B:
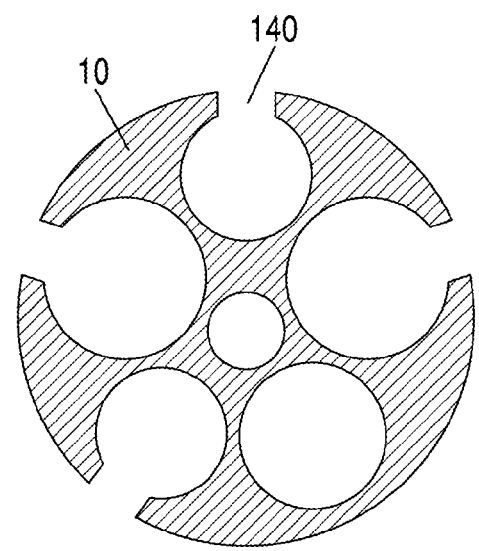
FIG. 22B illustrates a cross-sectional view of the catheter of FIG. 22A, according to an exemplary embodiment.
Figure 23A:
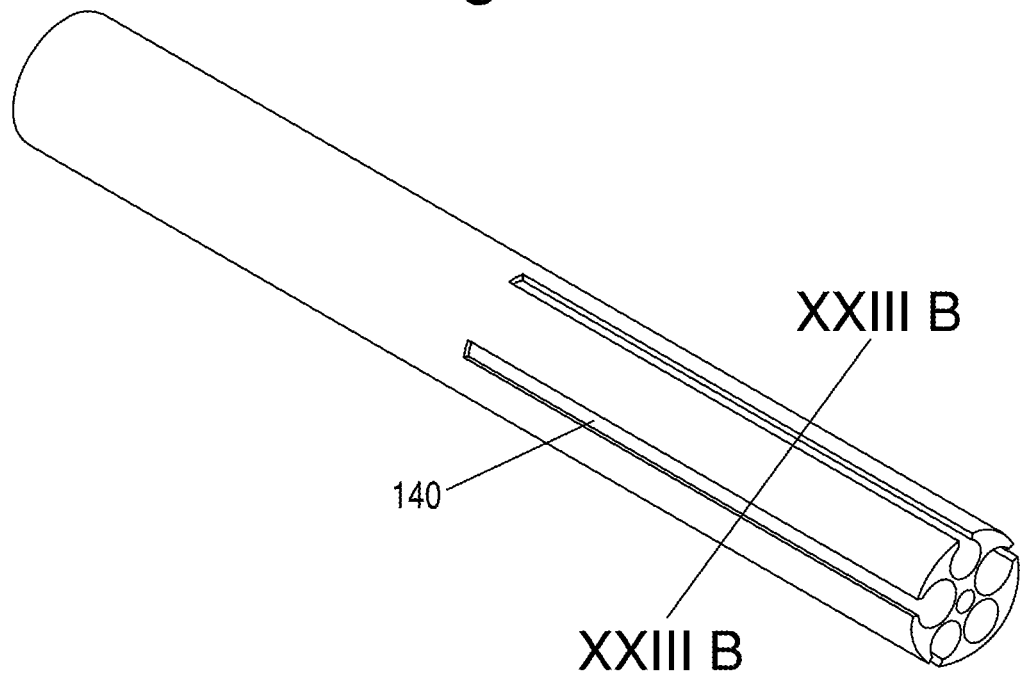
FIG. 23A illustrates a catheter having longitudinal slots along a portion of its length.
Figure 23B:
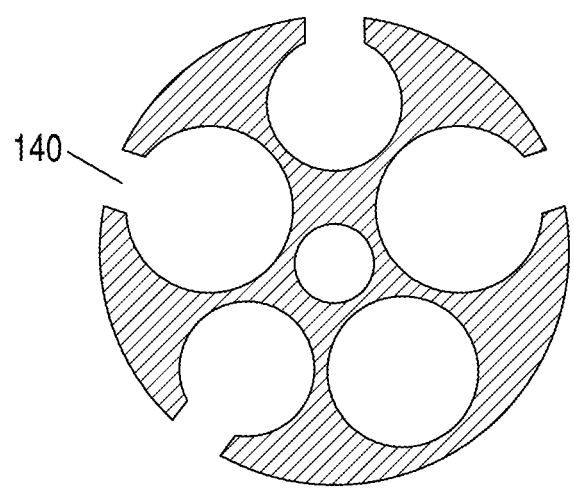
FIG. 23B illustrates a cross-sectional view of the catheter of FIG. 23A, according to an exemplary embodiment.
Figure 24A:
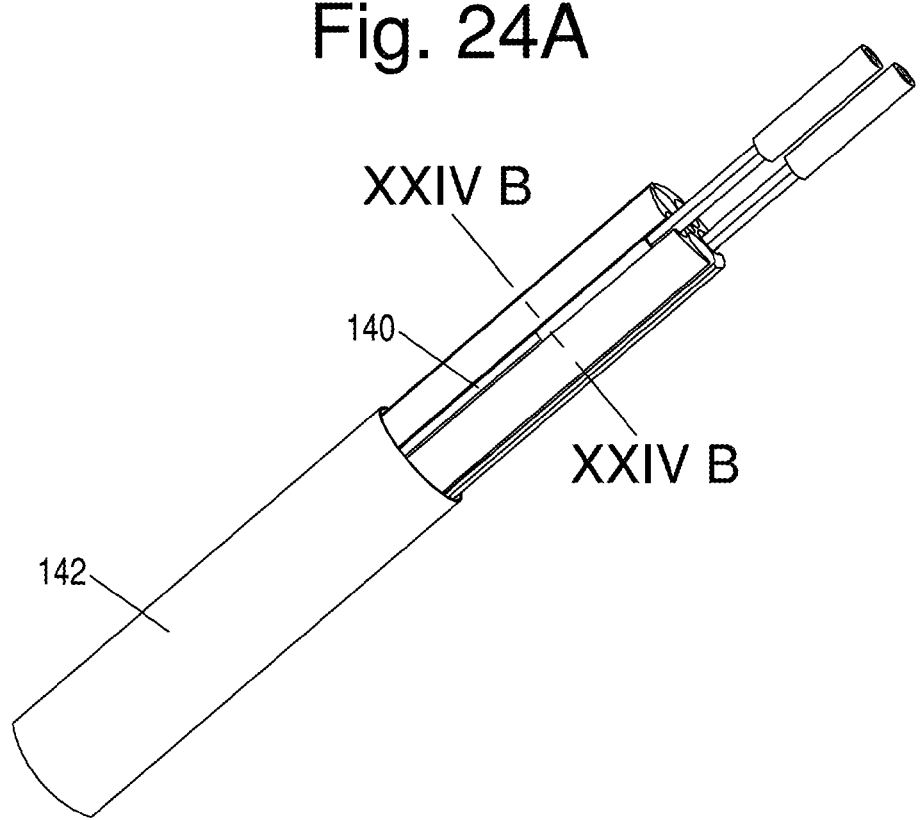
FIG. 24A illustrates electrode assemblies within the catheter of either FIGS. 22A-22B or 23A-23B, with a sleeve shown covering a portion of the catheter.
Figure 24B:
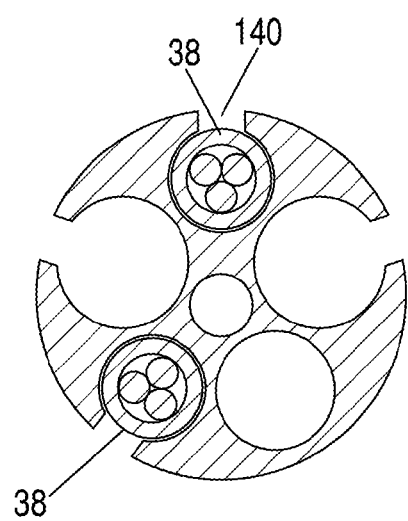
FIG. 24B illustrates a cross-sectional view of FIG. 24A, according to an exemplary embodiment.

Referring to FIGS. 22A-24B, in additional or alternative embodiments, the catheter 10 may include elongated openings 140 along the its exterior. The elongated openings 140 may connect the exterior of the catheter 10 to an interior lumen and may be referred to as slits or channels. As shown in FIGS. 22A-22B, the elongated openings 140 may extend along the full length of the catheter 10. Additionally or alternatively, as shown in FIGS. 23A-23B, the elongated openings 140 may extend along part of the length of the catheter 10. As shown in FIGS. 24A and 24B, the elongated openings 140 may additionally or alternatively be covered by a sleeve 142.

Threading electrode assemblies 32, 34 through the lumens of catheter 10 during assembly of medical device 50 may present challenges due to the length of the lumens and their small diameter. In the embodiments of FIGS. 22A-24B, the electrode assemblies 32, 34 may be inserted into one or more lumens of catheter 10 through elongated openings 140. The ability to access the lumens of the catheter 10 from locations radially outside of the lumens, rather than from the proximal and distal ends of the lumens, may simplify installation of electrical leads 44 and other components of the medical device 50 during the manufacturing process.

The elongated openings 140 may be created during an initial extrusion or molding process to form catheter 10 or may be created during a later step. Some non-limiting examples of suitable polymers for the first extrusion or molding are: low and high-density thermoplastic polyurethanes such as polyester, polyether, and polycarbonate-based varieties; polycarbonate-based polyurethanes; and polyamides (nylon) and polyamide block copolymers (PEBA).

As shown in FIGS. 24A and 24B, after the electrode assemblies 32, 34 are installed in the lumens of catheter 10, an outer sleeve 142 may be threaded over the catheter 10 to secure the wire assemblies within the lumens. The outer sleeve 142 may be a polymeric tubular sleeve and may be formed by extrusion. The inner diameter of the outer sleeve 142 may be large enough to slide over the outside of the catheter 10 but may be small enough to retain the electrode assemblies 32, 34 within the lumens of the catheter 10 after it has been slid over the catheter 10. The outer sleeve 142 may extend in a proximal-distal direction along a desired length of the catheter 10.

The outer sleeve 142 may be formed of a thin, thermoplastic material such as, but not limited to, polyamide, polyether block amide, polyurethane, silicone rubber, nylon, polyethylene, fluorinated hydrocarbon polymers, etc. Examples of polymer materials suitable for use in the sleeve are commercially available under the trademarks PEBAX™ and PELLETHANE™.

The outer sleeve 142 may be thermally bonded or otherwise mechanically attached to the catheter 10 by any of a number of methods. In one such method, a tubular member, which may be formed by extrusion, may be placed over and around both the catheter 10 and the outer sleeve 142. The tubular member may be shrinkable to compress against the outer sleeve 142. For example, the tubular member may comprise heat shrink tubing. The heat shrink tubing can be formed of one or more layers depending upon the desired properties. As an example, heat-shrink tubing from Parker TexLoc (Fort Worth, Tex.) has two layers for electrical insulation. Texflour fluoropolymer double-shrink heat shrinkable tubing has an outer layer of PTFE heat shrink with an inner layer of FEP tubing. When using double shrink tubing, the catheter 10 may be encapsulated by the FEP tubing as the PTFE shrinks, melting the FEP and creating a waterproof protective covering which is desirable for a variety of applications including RF and electrical stimulation devices.

Thermal energy then may be applied to the heat shrink tubing to compress the heat shrink tubing around the outer sleeve 142 and the catheter 10. Contraction of the heat shrink tubing provides a compressive force directed radially inward on the outer sleeve 142. The compressive force exerted by the heat shrink tubing helps secure the outer sleeve 142 to the catheter 10.

At the same time, or in a later step, thermal energy (e.g. RF heating, electromagnetic induction heating, etc.) may be applied to the assembly comprising the heat shrink tubing, the outer sleeve 142, and the catheter 10. The thermal energy may be sufficient to elevate the temperature of the assembly in order to induce bonding of the outer sleeve 142 to the catheter 10. The combination of the compressive force generated by the heat shrink tubing and the thermal energy heating the materials above their respective melt temperatures will serve to bond the outer sleeve 142 and the catheter 10 together. The thermal energy is typically not high enough to create a bond between the heat shrink tubing and the polymeric sleeve nor is it high enough to damage the integrity of the catheter assembly.

The heat shrink tubing may then be removed from the assembly comprising the catheter 10 (which is received inside the outer sleeve 142). A slit, notch, perforations, or other weakened regions may be used to assist with the removal of the heat shrink tubing from the assembly. In some cases, the shrink tubing may be constructed of a biocompatible material such as EPTFE and can be left on the catheter assembly.

Within lumens of catheter 10 according to any embodiments disclosed herein, it may be desirable to insert a support structure, such as a polytetrafluoroethylene (e.g., Teflon) coated mandrel, which may provide interior support to maintain the structure of the catheter 10 and preserve the patency of the longitudinal lumen throughout the manufacturing process. The support structure can later be removed by pulling it through either the distal or proximal openings in the lumen. In some cases the support structure can be stretched and elongated, thereby reducing its cross-sectional area, prior to removal.

One or more outer sleeves 142 of different materials, thicknesses, or material properties (e.g. durometer) can be used at various locations along the length of catheter 10 to alter various physical properties (e.g. stiffness, torqueability, friction, etc.) at specific locations along the length of the finished catheter. For example, a flexible sleeve 142 could be utilized at the distal portion of the catheter 10 to allow the tip of the catheter 10 to more easily track along a guidewire. A more rigid sleeve 142 could be used at the proximal portion of the catheter 10 to allow for more pushability or torqueability when grasping the distal end of the catheter 10. Adjacent sleeves 142 could be butt-welded or otherwise coupled end-to-end during the final forming process. Lap-joints or scarf joints may optionally be used to form a smoother transition between adjacent sleeves 142.

Other elements or structures may be incorporated into the catheter 10 construction using the assembly method described above. As one example, to help provide a desirable shape or contour to the distal end of the catheter 10, a shaping element may be inserted into one of the elongated openings 140, or into an enclosed lumen, at a desired location along the first extrusion. The shaping element may be formable or pre-formed to impart a desired configuration (e.g. a desired curvature) to the catheter 10. The shaping element may be pre-formed or formed to cause the catheter 10 to curve in a plane having a desired angular relationship, such as, for example, to aid in positioning electrodes 36, 38 of the medical device 50.

The shaping element may be resiliently flexible. In some embodiments, the shaping element may comprise a predetermined length of e.g. nitinol wire, ribbon, spring, etc. In some embodiments, the shaping element may comprise a temperature-dependent shape-memory material such as a shape-memory alloy. In some embodiments, the shaping element may be constructed to assume a desired shape after the catheter 10 has entered the body of a patient. For example, body heat may cause a shape-memory shaping element to change to a desired shaped configuration, or an external source of energy (e.g. an electrical current) may be applied to cause a shape change of a shaping element by a thermal or other mechanism. In some embodiments the shaping element becomes more curved upon actuation.

Alternative Lead Embodiments

Referring to FIGS. 25A-26H, in an additional or alternative embodiment, one or all of the electrode leads 44 may be embedded in a flexible ribbon cable 144. The ribbon cable 144 may include multiple insulated leads 44 connected along their lengths to form a single planar structure. The planar structure may be flexible to form other shapes. Similar to other leads 44 described herein, the leads 44 of the ribbon cable 144 may include an elongated conductive member 45 surrounded by a layer of non-conductive material 46, such as insulation.

Figure 25A:
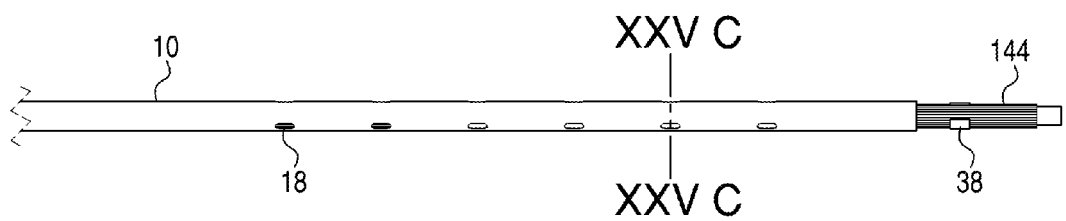
FIG. 25A illustrates a side view of a ribbon wire catheter with an inner catheter core and an outer insulation jacket.
Figure 25B:
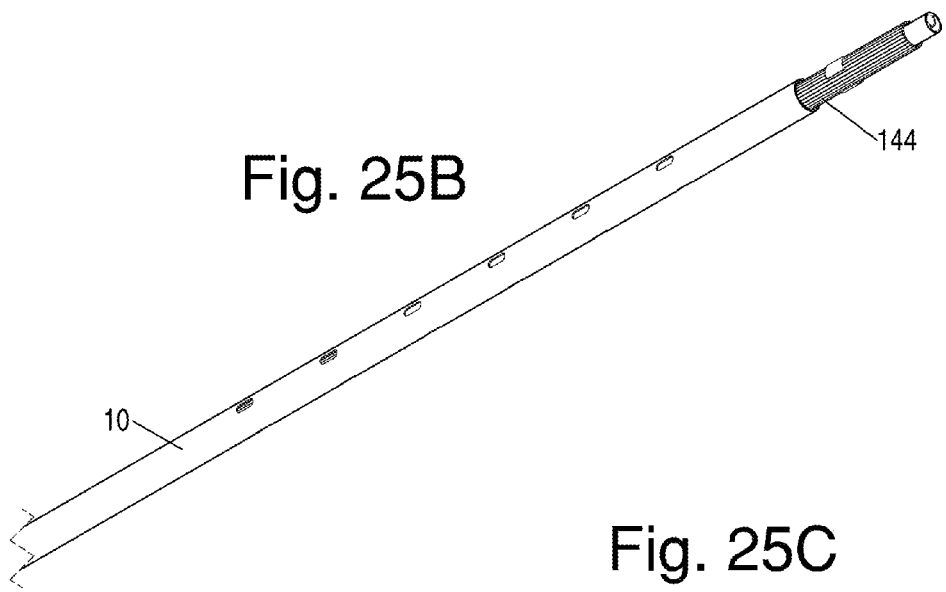
FIG. 25B illustrates a perspective view of the catheter of FIG. 25A.
Figure 25C:
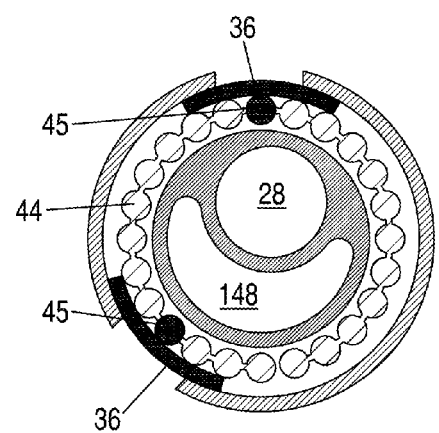
FIG. 25C illustrates a cross-sectional view of the catheter of FIG. 25A, according to an exemplary embodiment.

In the embodiment of FIGS. 25A-25C, the ribbon cable 144 may be closed as a flexible cylinder (e.g., formed around a mandrel and the approximated ribbon edges fixed with adhesive along the length). This design may allow any of the leads 44 to be deinsulated at a point along the catheter length and attached to an electrode 36, 38, such as, for example, a flexible foil electrode or an electrode formed according to any of the embodiments described herein. Two proximal electrodes 36 of the ribbon cable embodiment may be seen in the cross-section of FIG. 25C and will be described in greater detail below. The exterior elongated tubular member of catheter 10 may be formed around the ribbon cable 144 using the heat shrink method previously described to form a smooth electrically-insulating wall. Individual electrodes 36, 38 may be exposed through windows 18, 16 formed in the catheter 10, similar to other embodiments.

An advantage of the embodiment of FIGS. 25A-25C is that a larger portion of the entire catheter 10 cross-section may be available for guide wire and/or fluid lumen(s). As shown in FIG. 25C, the ribbon cable 144 may be supported by a support catheter 146, which may include the lumens described in connection with other embodiments or may include the guidewire lumen 28 and the delivery lumen 148 shown in FIG. 25C. Another advantage of the embodiment of FIGS. 25A-25C is its simplicity and ease of fabrication.

Figure 26D:
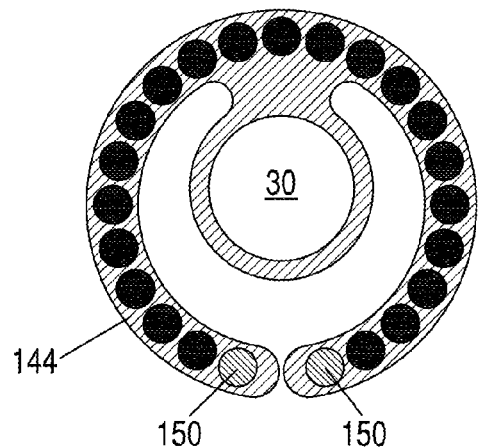
FIG. 26D illustrates the ribbon wire catheter of FIG. 26A, shown attached to a guidewire lumen and in a closed position.
Figure 26E:
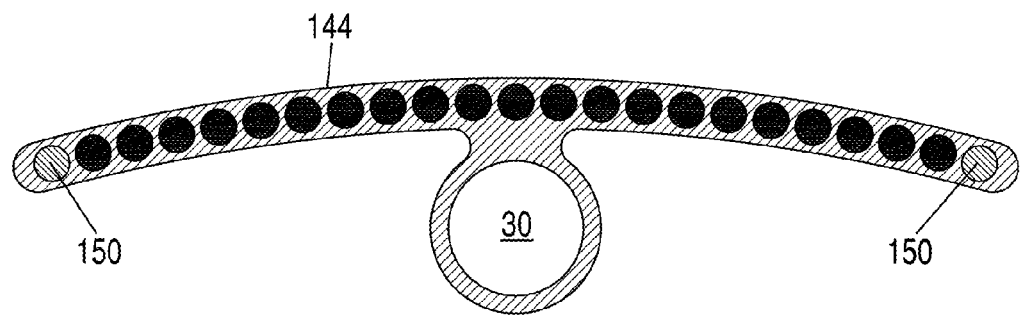
FIG. 26E illustrates the ribbon wire catheter of FIG. 26D in an open position.

FIGS. 26A-26H illustrate use of ribbon cable 144 in greater detail. Referring to FIG. 26B, proximal electrodes 36 may contact leads 44 within ribbon cable 144. Referring to FIG. 26C, distal electrodes 38 may contact different leads 44 within ribbon cable 144. The ribbon cable 144 may be held temporarily in a cylindrical form with a weak adhesive (such as an adhesive that dissolves in contact with blood, such as e.g., sucrose). As shown in FIGS. 26D and 26E, a guide wire lumen 30 or other lumens may be permanently attached to the ribbon cable 144 (for example using a strong biocompatible adhesive). The ribbon cable 144 and any support catheter 146 may be wrapped in a thin electrically-insulating covering to form catheter 10 (for example by sliding the assembly into a sleeve 142 and using the previously described heat-shrink method or the like). A seam may be opened (e.g. using a knife or laser) directly over the ribbon cable 144 seam to transition the ribbon cable 144 from the closed position shown in FIG. 26D to the open position shown in FIG. 26E. An adhesive may be used to transition the ribbon cable 144 from the position shown in FIG. 26E to the position shown in FIG. 26D. As in other embodiments, windows 16, 18 may be formed in the exterior covering of the catheter 10 to reveal electrodes 36, 38 at their desired locations.

A catheter 10 having a ribbon cable 144 may be introduced into a blood vessel of the body of a subject in its closed configuration (see FIG. 26D). Once inside the vessel, the adhesive may dissolve in a matter of several minutes and the ribbon cable 144 may be free to deploy into a nearly flat configuration, which may be its preferred state due to the natural elasticity of the ribbon cable 144. Optionally, two control members 150, such as Nitinol or other springy metal wires, or pull wires, may be embedded along the edges of the ribbon cable 144, and their natural elasticity and/or operation may contribute to the desired open configuration shown in FIG. 26E.

Figure 26F:
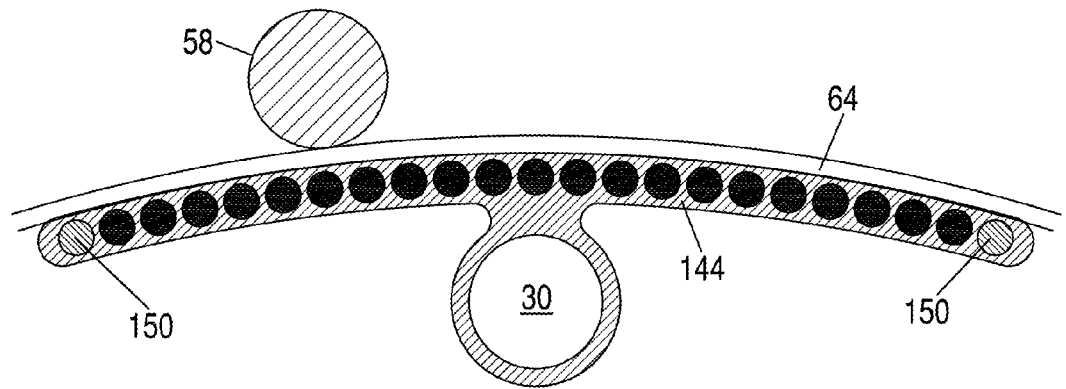
FIG. 26F illustrates the ribbon wire catheter of FIG. 26D in relation to a vessel wall and target nerve.

Referring to FIG. 26F, the natural elasticity of the ribbon cable 144 and/or the control members 150 may contribute to urge the ribbon cable 144 toward the vessel wall in such a way that the electrodes are proximate to the vessel wall in the vicinity of a target nerve, such as right phrenic nerve 58. With this design, one or more of the catheter electrodes 36, 38 exposed through windows 18, 16 is likely to be in very close proximity to the target nerve and may afford highly selective recruitment of the nerve with very low current or charge delivery. Furthermore, this design provides effective insulation of the electrodes 36, 38 from the blood in the vessel, thus minimizing current spread to unwanted regions and maximizing recruitment selectivity of the target nerve.

Figure 26G:
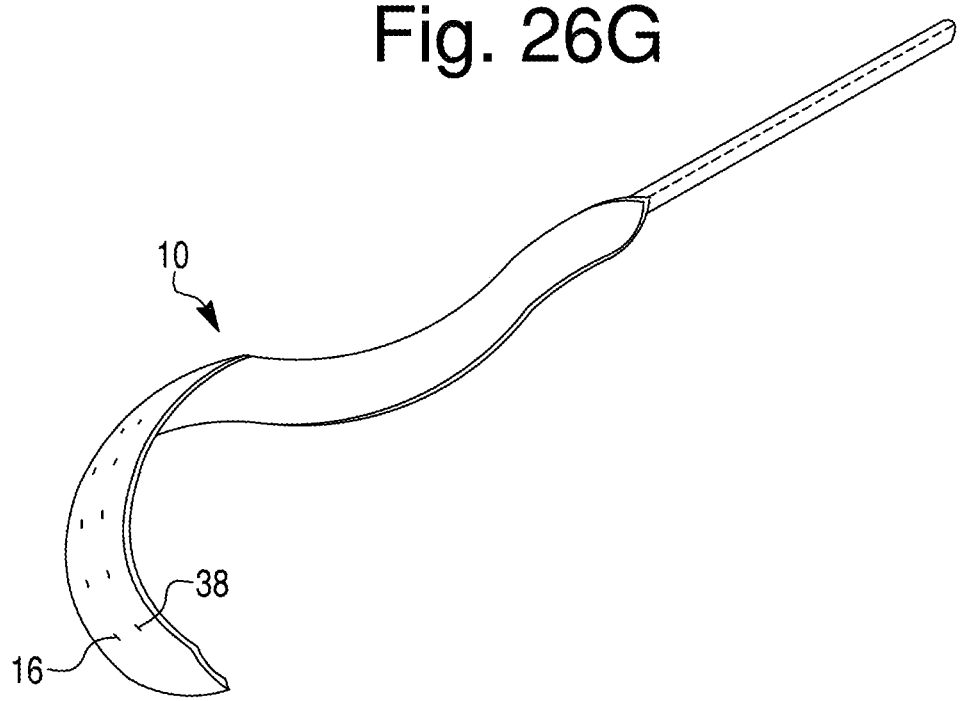
FIG. 26G illustrates a perspective view of the ribbon wire catheter of FIG. 26A in an open position.

FIG. 26G is an isometric view of a catheter 10 having a ribbon cable 144 intended for deployment inside a vessel. In this embodiment, the proximal portion of the catheter 10 may have a near-circular, tubular cross-section in regions where the ribbon cable 144 is adhered with permanent adhesive that will not dissolve in blood. In contrast, the distal portions of the catheter 10 are shown in FIG. 26G to have opened into the open ribbon cable configuration where the attachment of ribbon edges was temporary and the adhesive was dissolved once inside the blood vessel lumen. It is further seen in FIG. 26G that the distal portion of the catheter having a ribbon cable 144 may naturally adopt a corkscrew (or "helical") configuration, the dimensions of which are determined by the properties of the control members 150 embedded along the ribbon cable edges. One configuration may be a corkscrew section of approximately 20 mm diameter and approximately 30 mm length. Such a configuration may ensure that some of the distal wires are in close proximity with, for example, the target right phrenic nerve 58 coursing on the outside of the superior vena cava 64 (not shown in FIG. 24G but shown in FIG. 21).

Figure 26H:
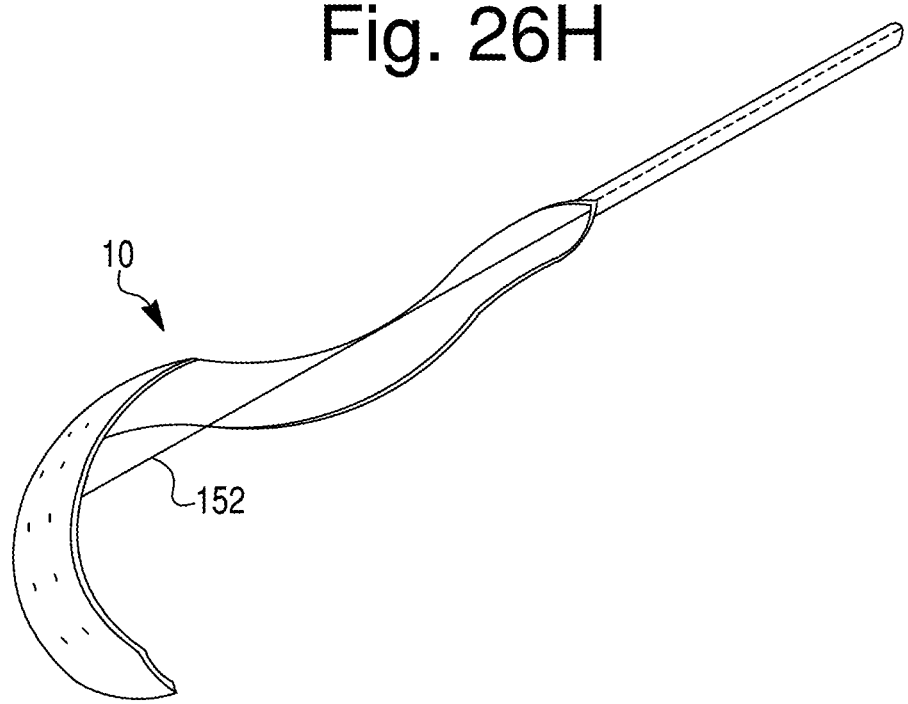
FIG. 26H illustrates the ribbon wire catheter of FIG. 26G with a pull wire, according to exemplary embodiments.

FIG. 26H illustrates a control member 152 that can be used to restrict the total length of the distal coiled portion of the catheter 10 having a ribbon cable 144. The control member 152 may be attached to a point near the distal end of the catheter 10 and may run freely through a lumen inside the proximal portion of the catheter, crossing to outside the patient where the proximal end of the pull wire can be controlled by the practitioner. By pulling on the control member 152, the catheter 10 having a ribbon cable 144 may be controlled to open maximally inside the SVC, ensuring that the ribbon surface is completely deployed against the vessel wall.

Medical Device Having a Barometer

The medical device 50 may include barometric correction that allows the device 50 to operate at different altitudes, since a patient receiving electrical stimulation phrenic-nerve pacing of the diaphragm may need to breathe a constant oxygen supply, but the density of air declines with altitude. The natural correction is for the patient to breathe more deeply and/or more rapidly to compensate. The medical device 50 or the catheter 10 may include a gauge (e.g. a barometer) that measures atmospheric pressure in order to compensate for altitude changes. High altitude performance is especially valuable to the military, any other agency transporting injured people (ski resorts, mountain climbers) and more generally, any patient who requires pacing and needs to travel in an aircraft.

Medical Device Equipped with Electronic Chip

The medical device 50 or the catheter 10 may be equipped with an electronic chip that stores information about the catheter 10 and/or its usage. The chip may be, for example, provided in a hub of the catheter 10. In one embodiment, when the catheter 10 is coupled to a controller, the controller may read the chip and send signals to the electrodes 36, 38 only if the chip has the correct encryption and/or makes a correct response etc. The chip may store information such as one or a plurality of the catheter serial number; size (length and/or diameter); lot number; batch number; date manufactured; electrode arrangement; electrode interconnection information (pin-outs for a connector connected to the electrodes by conductors in the catheter); etc. The controller may accept algorithm upgrades that only apply to certain serial numbers or catheter types determined with reference to the information stored in the chip.

Other Alternative Embodiments and Interpretation of Terms

As noted earlier, any of the components and features of any of the embodiments disclosed herein may be combined and used in any logical combinations with any of the other components and features disclosed herein. However, for the sake of example, some ways in which the described example embodiments may be varied include:
different numbers of electrodes;
different electrode configurations;
different electrode fixing (crimp, adhesive, microweld, etc.);
different electrode shape (round, oval, circular, rectangular, etc.);
different electrode material;
different electrode surface areas;

different electrode spacing;
different number or shapes of lumens;
different window shape/dimensions;
different catheter profile (e.g., +/−9Fr);
different catheter length; and/or
different steering mechanism.

Unless the context clearly requires otherwise, throughout the description and the claims:

"comprise," "comprising," and the like are to be construed in an inclusive sense, as opposed to an exclusive or exhaustive sense; that is to say, in the sense of "including, but not limited to";

"connected," "coupled," or any variant thereof, means any connection or coupling, either direct or indirect, between two or more elements; the coupling or connection between the elements can be physical, logical, or a combination thereof;

"herein," "above," "below," and words of similar import, when used to describe this specification, shall refer to this specification as a whole, and not to any particular portions of this specification;

"or," in reference to a list of two or more items, covers all of the following interpretations of the word: any of the items in the list, all of the items in the list, and any combination of the items in the list; and the singular forms "a," "an," and "the" also include the meaning of any appropriate plural forms.

Words that indicate directions such as "vertical," "transverse," "horizontal," "upward," "downward," "forward," "backward," "inward," "outward," "left," "right," "front," "back," "top," "bottom," "below," "above," "under," and the like, used in this description and any accompanying claims (where present), depend on the specific orientation of the apparatus described and illustrated. The subject matter described herein may assume various alternative orientations. Accordingly, these directional terms are not strictly defined and should not be interpreted narrowly.

Specific examples of systems, methods and apparatus have been described herein for purposes of illustration. These are only examples. The technology provided herein can be applied to systems other than the example systems described above. Many alterations, modifications, additions, omissions, and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

It is therefore intended that the following appended claims and claims hereafter introduced are interpreted to include all such modifications, permutations, additions, omissions, and sub-combinations as may reasonably be inferred. The scope of the claims should not be limited by the preferred embodiments set forth in the examples, but should be given the broadest interpretation consistent with the description as a whole.

We claim:

1. A nerve stimulation system, comprising:
   a signal generator; and
   a catheter comprising:
      a plurality of lumens extending from a proximal end of the catheter to a distal end of the catheter;
      a plurality of proximal electrodes positioned on an exterior surface of a catheter;
      a plurality of distal electrodes positioned on the exterior surface of the catheter; and
      a first plurality of electrical leads positioned on the exterior surface of the catheter and connecting the plurality of proximal electrodes to the signal generator, and a second plurality of electrical leads distinct from the first plurality of leads, positioned on the exterior surface of the catheter, and connecting the plurality of distal electrodes to the signal generator,
   wherein the proximal electrodes are configured to be positioned in a venous system of a patient to stimulate a left phrenic nerve, and the distal electrodes are configured to be positioned in a venous system of a patient to stimulate a right phrenic nerve,
   wherein a row of the plurality of distal electrodes extends along a first axis and along a first length of the catheter, the first axis being parallel to a longitudinal axis of the catheter, and
   wherein a row of the plurality of proximal electrodes extends along a second axis and along a second length of the catheter, the second axis being parallel to the longitudinal axis of the catheter, and
   wherein the first length of the catheter is without stimulation electrodes along the second axis, and the second length of the catheter is without stimulation electrodes along the first axis.

2. The nerve stimulation system of claim 1, wherein the plurality of proximal electrodes, the plurality of distal electrodes, the first plurality of electrical leads, and the second plurality of electrical leads are printed onto the exterior surface of the catheter.

3. The nerve stimulation system of claim 1, wherein the plurality of proximal electrodes, the plurality of distal electrodes, the first plurality of electrical leads, and the second plurality of electrical leads include a conductive ink.

4. The nerve stimulation system of claim 1, wherein at least one lumen of the plurality of lumens includes a tool, and wherein at least some of the first plurality of electrical leads are circumferentially offset from at least some of the second plurality of electrical leads.

5. The nerve stimulation system of claim 1, wherein at least one lumen of the plurality of lumens is configured to at least one of deliver fluid to or remove fluid from a patient.

6. The nerve stimulation system of claim 1, wherein the plurality of proximal electrodes are configured to be positioned in at least one of a left jugular vein or a left subclavian vein, and the plurality of distal electrodes are configured to be positioned in a superior vena cava.

7. The nerve stimulation system of claim 1, wherein a distance between the proximal electrodes and the distal electrodes along the catheter is so that, when the proximal electrodes are positioned in the venous system to stimulate the left phrenic nerve, the distal electrodes are positioned in the venous system to stimulate the right phrenic nerve.

8. A method for nerve stimulation using a nerve stimulation system having a signal generator and a catheter, the method comprising:
   positioning the catheter in a venous system of a patient, the catheter comprising:
      a plurality of lumens extending from a proximal end of the catheter to a distal end of the catheter;
      a plurality of proximal electrodes positioned on an exterior surface of the catheter;
      a plurality of distal electrodes positioned on the exterior surface of the catheter, wherein:

a row of the plurality of distal electrodes extends along a first axis and along a first length of the catheter, the first axis being parallel to a longitudinal axis of the catheter, a row of the plurality of proximal electrodes extends along a second axis and along a second length of the catheter, the second axis being parallel to the longitudinal axis of the catheter, and the second length of the catheter is without stimulation electrodes along the first axis; and a plurality of electrical leads positioned on the exterior surface of the catheter and connecting the plurality of proximal electrodes and the plurality of distal electrodes to the signal generator;

stimulating a left phrenic nerve with a first electrode combination of the plurality of proximal electrodes; and stimulating a right phrenic nerve with a second electrode combination of the plurality of distal electrodes.

9. The method of claim 8, wherein the plurality of proximal electrodes, the plurality of distal electrodes, and the plurality of electrical leads are printed onto the exterior surface of the catheter.

10. The method of claim 8, wherein the plurality of proximal electrodes, the plurality of distal electrodes, and the plurality of electrical leads include a conductive ink.

11. The method of claim 8, further comprising:
positioning the plurality of proximal electrodes in at least one of a left jugular vein or a left subclavian vein; and
positioning the plurality of distal electrodes in a superior vena cava.

12. The method of claim 8, further comprising at least one of delivering fluid to or removing fluid from a patient through one of the plurality of lumens.

13. The method of claim 8, wherein the first electrode combination includes a bipolar pair of electrodes, and the second electrode combination includes a bipolar pair of electrodes.

14. The method of claim 8, further comprising:
testing a plurality of pairs of electrodes of the plurality of proximal electrodes to select the first electrode combination; and
testing a plurality of pairs of electrodes of the plurality of distal electrodes to select the second electrode combination.

15. A nerve stimulation system, comprising:
a signal generator;
a catheter comprising:
a plurality of lumens extending from a proximal end of the catheter to a distal end of the catheter;
a plurality of electrodes each printed on only a portion of a circumference of the catheter, wherein the plurality of electrodes includes proximal electrodes and distal electrodes; and
a plurality of electrical leads printed on the catheter and connecting the plurality of electrodes to the signal generator, wherein each lead of the plurality of electrical leads that is connected to a corresponding distal electrode of the distal electrodes extends past the proximal electrodes, without contacting the proximal electrodes;
wherein the signal generator is configured to send electrical signals to an electrode combination of the plurality of electrodes for stimulation of a phrenic nerve·
wherein a row of the distal electrodes extends along a first axis and along a first length of the catheter, the first axis being parallel to a longitudinal axis of the catheter,
wherein a row of the proximal electrodes extends along a second axis and along a second length of the catheter, the second axis being parallel to the longitudinal axis of the catheter, and
wherein the first length of the catheter is without stimulation electrodes along the second axis, and the second length of the catheter is without stimulation electrodes along the first axis.

16. The nerve stimulation system of claim 15, wherein the plurality of electrodes and the plurality of electrical leads include a conductive ink, and wherein at least a portion of the plurality of electrical leads is covered with an insulative material.

17. The nerve stimulation system of claim 15, wherein, the electrode combination of the plurality of electrodes is an electrode combination of the plurality of proximal electrodes, and the phrenic nerve is a left phrenic nerve; and wherein the signal generator is further configured to send electrical signals to an electrode combination of the plurality of distal electrodes for stimulation of a right phrenic nerve.

18. The nerve stimulation system of claim 17, wherein the plurality of proximal electrodes are configured to be positioned in at least one of a left jugular vein or a left subclavian vein, and the plurality of distal electrodes are configured to be positioned in a superior vena cava.

19. The nerve stimulation system of claim 15, further comprising a tool in at least one of the plurality of lumens.

* * * * *